(12) United States Patent
Pilyugina

(10) Patent No.: US 10,272,418 B2
(45) Date of Patent: Apr. 30, 2019

(54) MESOPOROUS ZEOLITES AND METHODS FOR THE SYNTHESIS THEREOF

(71) Applicant: Saudi Arabian Oil Company, Dhahran (SA)

(72) Inventor: Tatiana Pilyugina, Waltham, MA (US)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 15/670,686

(22) Filed: Aug. 7, 2017

(65) Prior Publication Data

US 2019/0039054 A1  Feb. 7, 2019

(51) Int. Cl.
*C01B 39/48* (2006.01)
*C01B 39/20* (2006.01)
(Continued)

(52) U.S. Cl.
CPC ............. *B01J 29/06* (2013.01); *B01J 29/041* (2013.01); *B01J 29/08* (2013.01); *B01J 29/18* (2013.01);
(Continued)

(58) Field of Classification Search
CPC ....... C01B 39/24; C01B 39/265; C01B 39/36; C01B 39/40; C01B 39/205; C01B 39/48; C01P 2006/14; C01P 2006/16; C01P 2006/17; B01J 29/041; B01J 29/084; B01J 29/18; B01J 29/40; B01J 37/082;
(Continued)

(56) References Cited

U.S. PATENT DOCUMENTS

| 3,972,983 A | 8/1976 | Ciric | |
|---|---|---|---|
| 8,623,237 B2 * | 1/2014 | MacLachlan | ...... B01D 67/0048 |
| | | | 252/299.01 |

FOREIGN PATENT DOCUMENTS

| CN | 102190316 B | 1/2013 |
|---|---|---|
| CN | 102295297 B | 6/2013 |

(Continued)

OTHER PUBLICATIONS

Kresge et al, "Ordered mesoporous molecular sieves sythesized by a liquid-crystal template mechanism", Nature, vol. 359, pp. 710-712 (Oct. 1992) (Year: 1992).*

(Continued)

*Primary Examiner* — David M Brunsman
(74) *Attorney, Agent, or Firm* — Dinsmore & Shol LLP

(57) ABSTRACT

Methods for producing mesoporous zeolites are provided. In some embodiments, the method includes mixing a silicon-containing material, an aluminum-containing material, or both, with a quaternary amine and at least one base to produce a zeolite precursor solution. The zeolite precursor solution is combined with nanocellulose to form a zeolite precursor gel, from which volatiles are removed. The zeolite precursor gel is crystallized to produce a crystalline zeolite intermediate. The crystalline zeolite intermediate is calcined to form the mesoporous zeolite. The nanocellulose mesopores template may include cellulose nanocrystals, nanocellulose fibers, or combinations thereof. The quaternary amine may include tetraethylammonium hydroxide, tetraethylammonium alkoxide, tetrapropylammonium alkoxide, other alkaline materials comprising ammonium, or combinations thereof.

26 Claims, 7 Drawing Sheets

(51) Int. Cl.

| | |
|---|---|
| C01B 39/26 | (2006.01) |
| C01B 39/40 | (2006.01) |
| B01J 29/04 | (2006.01) |
| B01J 29/06 | (2006.01) |
| B01J 29/08 | (2006.01) |
| B01J 29/18 | (2006.01) |
| B01J 29/40 | (2006.01) |
| B01J 29/70 | (2006.01) |
| C07C 211/62 | (2006.01) |
| C01C 1/04 | (2006.01) |
| C01B 39/36 | (2006.01) |
| G01N 23/20 | (2018.01) |
| B01J 37/08 | (2006.01) |

(52) U.S. Cl.
CPC .......... *B01J 29/40* (2013.01); *B01J 29/7007* (2013.01); *C01B 39/205* (2013.01); *C01B 39/265* (2013.01); *C01B 39/36* (2013.01); *C01B 39/40* (2013.01); *C01B 39/48* (2013.01); *C01C 1/04* (2013.01); *C07C 211/62* (2013.01); *B01J 37/08* (2013.01); *C01P 2006/16* (2013.01); *G01N 23/20* (2013.01)

(58) Field of Classification Search
CPC ................ B01J 35/1019; B01J 35/1023; B01J 35/1038; B01J 35/1057; B01J 35/1061; B01J 35/109; B01J 29/06; B01J 29/7007
See application file for complete search history.

(56) References Cited

FOREIGN PATENT DOCUMENTS

| CN | 105153819 A | 12/2015 |
|---|---|---|
| WO | 2013/188729 A1 | 12/2013 |

OTHER PUBLICATIONS

Tao et al,"Sunthesis of mesoporous zeolite single crystals with cheap porogens", Journal of Solid State Chemistry,m 184 (2011) 1820-1827 (Year: 2011).*
Aguado et al., Zeolite beta with hierarchical porosity prepared from organofunctionalized seeds, Microporous and Mesoporous Materials, 2008, 504-513, vol. 115, ScienceDirect.
Blaker et al., Renewable (greener) nanocomposite polymer foams synthesised from Pickering emulsion templates; Abstracts of Papers, 237th ACS National Meeting, Mar. 22-26, 2009; Salt Lake City, Utah.
Chal et al., Overview and industrial assessment of synthesis strategies towards zeolites and mesopores, ChemCatChem, 2011, 67-81, vol. 3, Wiley-VCH Verlag.
Chen et al., Synthesis and Photocatalytic Activity of Mesoporous TiO2 Using Nano-Cellulose Template Prepared by Acid Method; Chinese Journal of Inorganic Chemistry, 2013, 528-536, vol. 29, No. 3; Chinese Journal of Inorganic Chemistry.
Chen et al., An ordered, extra-large mesoporous ceramic acid with strong Brönsted acid sites and excellent thermal/hydrothermal stability, Chem. Commun., 2014, 3457-3459, vol. 50, The Royal Society of Chemistry.
Choi et al., A facile approach for the preparation of tunable acid nano-catalysts with a hierarchically mesoporous structure, Chem. Commun., 2014, 7652-7655, vol. 50, The Royal Society of Chemistry.
Choi et al., Amphiphilic organosilane-directed synthesis of crystalline zeolite with tunable mesoporosity, Nature Materials, 2006, 718-723, vol. 5, Nature Publishing Group.
Dufresne, Nanocellulose: A new ageless bionanomaterial, Materials Today, 2013, 1-17, vol. 16(6), Elsevier Ltd.

Egeblad et al.,Templating Mesoporous Zeolites, Chem. Mater., 2008, 946-960, vol. 20, American Chemical Society.
Gao et al., Self-Asembly of Nanocellulose and Indomethacin into Hierarchically Ordered Structures with High Encapsulation Efficiency for Sustained Release Applications, ChemPlusChem; 2014, 725-731, vol. 79, Wiley-Verlag GmbH& Co, Weinheim.
Habib et al., Key advances in the chemical modification of nanocelluloses, Chemical Soc. Rev., 2014, 1519-1542, vol. 43, The Royal Society of Chemistry.
Hakalahti et al., Direct Interfacial Modification of Nanocellulose Films for Thermoresponsive Membrane Templates; ACS Applied Materials and Interfaces; 2016, 2923-2927, vol. 8, American Chemical Society.
Henry et al., Conversion of Nanocellulose Aerogel into TiO2 and TiO2@C Nanothorns by Direct Anhydrous Mineralization with TiCl4. Evaluation of Electrochemical Properties in Li Batteries, ACS Applied Materials & Interfaces, 2015, 14584-14592, vol. 7, American Chemical Society.
Ikhuoria, et al., Nanocellulose Crystals from Coir Fibre for Template Application; American Chemical Science Journal; 2015, Article No. ACSJ.18766, Science Domain.
Ivanova et al., Nanocellulose-Assisted Formation of Porous Hematite Nanostructures; Inorganic Chemistry; 2015, 1129-1135, vol. 54; American Chemical Society.
Ivanova et al., Nanocellulose-Templated Porous Titania Scaffolds Incorporating Presynthesized Titania Nanocrystals, Chemistry of Materials, 2015, 6205-6212, vol. 27, American Chemical Society.
Keshavarzi et al., Nanocellulose-Zeolite Composite Films for Odor Elimination; Applied Materials and Interfaces; 2015, 14254-14262, vol. 7, American Chemical Society.
Koo et al., Direct synthesis of carbon-templating mesoporous ZSM-5 using microwave heating; Journal of Catalysis, 2010, 327-334, vol. 276(2), Elsevier Inc.
Korhonen et al., Inorganic Hollow Nanotube Aerogels by Atomic Layer Deposition onto Native Nanocellulose Templates; American Chemical Society; 2011, 1967-1974, vol. 5, No. 3; ascnano.org.
Li et al., High Yield Preparation Method of Thermally Stable Cellulose Nanofibers, BioResources, 2014, 1986-1997, vol. 9(2), BioResources.com.
Li et al., Realizing the Commercial Potential of Hierarchical Zeolites: New Opportunities in Catalytic Cracking; ChemCatChem., 2014, 46-66, vol. 6(1), Wiley-VCH Verlag.
Lin et al, Preparation, properties and applications of polysaccharide nanocrystals in advanced functional nanomaterials: a review, Nanoscale, 2012, 3274-3294, vol. 4, The Royal Society of Chemistry.
Lu et al., Tunable morphologies of indium tin oxide nanostructures using nanocellulose templates; RSC Adv., 2015, 103680-103685, vol. 5, The Royal Society of Chemistry.
Luo et al., Nanocellulose as a template for a long-life anode material for rechargeable sodium-ion batteries; Cellulose Structures, Surfaces and Interfaces: Towards Truly Nanostructured Materials; 2014, Abstract, Dallas, Texas.
Menchaca-Nal et al., Facile synthesis of cobalt ferrite nanotubes using bacterial nanocellulose as template; Carbohydrate Polymers; 2016, 726-731, vol. 137; Elsevier Ltd.
Meng et al., Templating route for synthesizing mesoporous zeolites with improved catalytic properties; Nano Today; 2009, 292-301, vol. 4(4); Elsevier Ltd.
Moeller et al, One-Step Synthesis of Hierarchical Zeolite Beta via Network formation of Uniform Nanocrystals; Journal of the American Chemical Society; 2011, 5284-5295, vol. 133; American Chemical Society.
Möller et al, Mesoporosity—a new dimension for zeolites, Chemical Society Review, 2013, 3689-3707, vol. 42, The Royal Society of Chemistry.
Lopez-Orozco et al., Zeolitic Materials with Hierarchical Porous Structures; Advanced Materials; 2011, 2602-2615, vol. 23; Wiley-VCH.
Paako et al., Flexible and hierarchically porous nanocellulose aerogels: Templates for functionalities, Micro and Nanofibers from Sustainable Materials, Article, Mar. 23, 2010, ACS.

(56) References Cited

OTHER PUBLICATIONS

Park et al., Flexible conductive nanocellulose combined with silicon nanoparticles and polyaniline, Carbohydrate Polymers; 2016, 43-50, vol. 140; Elsevier Ltd.

Torres-Rendon et al., Bioactive Gyroid Scaffolds Formed by Sacrificial Templating of Nanocellulose and Nanochitin Hydrogels as Instructive Platforms for Biomimetic Tissue Engineering; Advanced Materials; 2015, 2989-2995, vol. 27; Wiley-VCH.

Serrano et al., Effect of the organic moiety nature on the synthesis of hierarchical ZSM-5 from silanized protozeolitic units, Journal of Materials Chemistry, 2008, 4210-4218, vol. 18, The Royal Society of Chemistry.

Serrano et al., Hierarchical ZSM-5 zeolites synthesized by silanization of protozeolitic units; Mediating the mesoporosity contribution by changing the organosilane type, Catalysis Today, 2014, 15-25, vol. 227, Elsevier Inc.

Serrano et al., Improvement of the hierarchical TS-1 properties by silanization of protozeolitic units in presence of alcohols, Microporous and Mesoporous Materials, 2013, 59-66, vol. 166, Elsevier Inc.

Shopsowitz et al., Biopolymer Templates Glass with a Twist: Controlling the Chirality, Porosity, and Photonic Properties of Silica with Cellulose Nanocrystals, Advanced Functional Materials Journal, 2014, 327-338, vol. 24, Wiley-VCH.

Tan et al., Interview-Exxon starts world's 1st crude-cracking petrochemical unit, Reuters, 2014, 1-3, Singapore, Reuters.

Tao et al., Synthesis of mesoporous zeolite single crystals with cheap porogens, Journal of Solid State Chemistry; 2011, 1820-1827, vol. 184, Elsevier Inc.

Tenhunen; et al., Significance of xylan on the stability and water interactions of cellulosic nanofibrils, Reactive & Functional Polymers, 2014, 157-166, vol. 85; Elsevier B.V.

Tian et al., Magnetic $Cu0.5Coo.5Fe2O4$ ferrite nanoparticles immobilized in situ on the surfaces of cellulose nanocrystals; Cellulose; 2015, 2571-2587, vol. 22; Springer Science.

Tingaut et al., Cellulose nanocrystals and microfibrillated cellulose as building blocks for the design of hierarchical functional materials, Journal of Materials Chemistry, 2012, 20105-20111, vol. 22, The Royal Society of Chemistry.

Wang et al., MFI Zeolite with Small and Uniform Intracrystal Mesopores**, Angewande Chemie, 2006, 7603-7606, vol. 45, Wiley VCH-Verlag.

White et al., A Sustainable Template for Mesoporous Zeolite Synthesis; Journal of the American Chemical Society; 2014, 2715-2718, vol. 136; American Chemical Society.

Zhu et al., Mesoporous zeolites as efficient catalysts for oil refining and natural gas conversion; Front. Chemi. Sci. Eng., 2013, 233-248, vol. 7(2); Higher Education Press and Springer-Verlag Berlin Heidelberg.

Qiu et al., Different Roles of CNTs in Hierarchical HZSM-5 Synthesis with Hydrothermal and Steam-Assisted Crystallization, RSC Adv., 2015, vol. 5(95), 78238-78246; Royal Society of Chemistry.

International Search Report and Written Opinion dated Dec. 15, 2017 for PCT/US2017/050654 Filed Sep. 8, 2017. pp. 1-11.

* cited by examiner

MESOPOROUS ZEOLITES AND METHODS FOR THE SYNTHESIS THEREOF

TECHNICAL FIELD

The present disclosure generally relates to mesoporous zeolites and methods of making mesoporous zeolites. Specifically, the present disclosure relates to mesoporous zeolites and methods of making mesoporous zeolites that may be utilized in the synthesis of porous catalytic materials.

BACKGROUND

Zeolites are aluminosilicate minerals that are exceedingly useful in a variety of applications, including oil refining, sorption and separation processes, as size-/shape-selective heterogeneous catalysts, as encapsulators, as slow-release agents, and in ion-exchanges, to name a few. However, the pore size of most zeolites (less than 0.74 nanometers in diameter) often limits the use of zeolites in many applications.

In petroleum processes, upgrading or "cracking" hydrocarbons is often used to refine crude oil and other high molecular weight hydrocarbons into much more valuable, smaller "light" hydrocarbons, such as gasoline and olefinic gases. One of the most common upgrading techniques is catalytic cracking, in which catalysts, most commonly conventional zeolite catalysts, are used to upgrade the hydrocarbons. However, due to the small pore size, (<20 Å), high molecular weight hydrocarbons must first undergo distillation and thermal cracking prior to catalytic cracking. Thermal cracking requires significant energy consumption and these additional steps increase the time and cost of the oil refining process.

While mesoporous silicas may provide a larger pore size, eliminating the preconditioning steps, silica-based materials lack the necessary acidity imparted by zeolites and, as such, have reduced catalytic activity. Moreover, attempts to increase acidity by incorporating the heteroatoms found in zeolites (such as aluminum), results in structure destabilization, as a significant percentage of silicon atoms in the framework must be removed.

SUMMARY

Accordingly, a need exists for mesoporous zeolite catalysts with a stabilized structure and improved catalytic activity.

In accordance with one embodiment of the present disclosure, a method for producing a mesoporous zeolite is provided. The method includes mixing a silicon-containing material, an aluminum-containing material, or both, with a quaternary amine and an alkali metal hydroxide to produce a zeolite precursor solution. The zeolite precursor solution is combined with nanocellulose to form a zeolite precursor gel, and the volatiles are removed. The dry zeolite precursor gel is crystallized in the presence of steam to produce a crystalline zeolite intermediate. The crystalline zeolite intermediate is calcined to form the mesoporous zeolite.

According to another embodiment, a mesoporous zeolite may be produced by a method wherein the nanocellulose mesopore template comprises at least one of cellulose nanocrystals, nanocellulose fibers, or combinations thereof, the crystallization comprises contacting the zeolite precursor gel with steam, and the crystalline zeolite intermediate is calcined by exposure to a temperature of at least 500° C.

Additional features and advantages of the technology disclosed in this disclosure will be set forth in the detailed description which follows, and in part will be readily apparent to those skilled in the art from the description or recognized by practicing the technology as described in this disclosure, including the detailed description which follows, the claims, as well as the appended drawings.

BRIEF DESCRIPTION OF THE DRAWINGS

The following detailed description of specific embodiments of the present disclosure can be best understood when read in conjunction with the following drawings, where like structure is indicated with like reference numerals and in which.

Reference will now be made in greater detail to various embodiments, some embodiments of which are illustrated in the accompanying drawings. Whenever possible, the same reference numerals will be used throughout the drawings to refer to the same or similar parts.

DETAILED DESCRIPTION

Figure 1A:
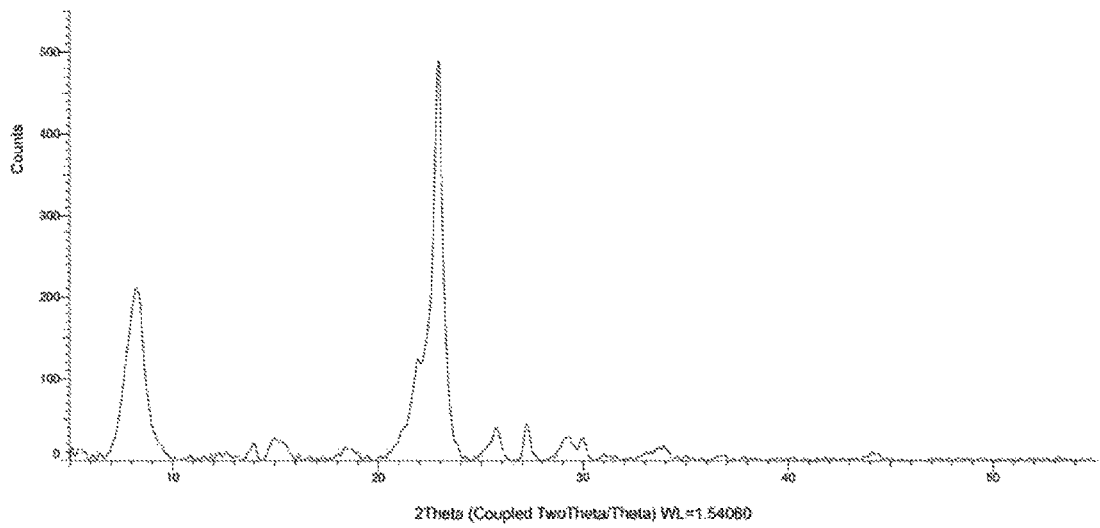
FIG. 1A is an x-ray diffraction ("XRD") graph of Example 1, according to embodiments shown and described herein.

This disclosure is directed to various embodiments of materials that may be used as structure-directing agents (SDAs) or mesopore templates for the fabrication of mesoporous zeolite materials. As used throughout this disclosure, a "zeolite material" or "zeolites" refers to inorganic materials with regular intra-crystalline cavities and channels of molecular dimension. The porous structure of zeolites may render large surface areas and desirable size-/shape-selectivity, which may be advantageous for catalysis. The mesoporous zeolites described may include aluminosilicates, titanosilicates, or pure silicates. As used throughout this disclosure, "mesopores" or "mesoporous" refers to pores in a structure that have a diameter of greater than 2 nanometers (nm) and less than or equal to 50 nm. Similarly, as used throughout the disclosure, "micropore" or "microporous" refers to pores in a structure that have a diameter of less than or equal to 2 nm and greater than or equal to 0.1 nm.

In some embodiments, nanocellulose mesopores templates may be used to produce the mesoporous zeolites. As used throughout this disclosure, the prefix "nano" (such as nanocellulose or nanofibers) refers to a component having an average size, such as an average length, width, or diameter, of from 0.1 to 500 nm. Specifically, the term "nanocellulose" refers to one or more of cellulose nanofibers, bacterial nanocellulose, or cellulose nanocrystals, which may generally, on average, have a width of from 3 to 50 nm (cellulose nanofibers), 20 to 100 nm (bacterial nanocellulose) or 3 to 20 nm (cellulose nanocrystals) and a length of 0.5 to 5 micrometers (μm) (cellulose nanofibers), 1 to 5 μm (bacterial nanocellulose) or 50 to 100 nm (cellulose nanocrystals).

Embodiments of the present disclosure relate to methods for producing mesoporous zeolites. The methods include mixing at least one of a material containing silicon or a material containing aluminum with a quaternary amine and alkali metal hydroxide to create a zeolite precursor solution. The zeolite precursor solution may contain the materials that form the porous structures, such as silicon-containing materials, aluminum-containing materials, or both. In one or more embodiments, the silicon-containing materials comprise silica ($SiO_2$), sodium silicate, tetramethylsiloxane, tetraethylsiloxane, silicate salt, silicon alkoxide, or combinations thereof. In one or more embodiments, the aluminum-containing materials comprise alumina ($Al_2O_3$), aluminum nitrate, aluminum sulfate, aluminum alkoxide, other aluminum salts, or combinations thereof.

In embodiments, a zeolite precursor solution may be combined with a nanocellulose mesopores template to form a zeolite precursor gel. In one or more embodiments, the nanocellulose mesopore template comprises nanocrystals, nanocellulose fibers, or combinations thereof. In embodiments, the precursor gel may then be crystallized to produce a crystalline zeolite intermediate. In one or more embodiments, the method may further comprise removing at least a solvent from the precursor gel prior to crystallization. The removing of at least a solvent may be done either actively or passively. In some embodiments, one such solvent is water. In embodiments, the crystallization comprises contacting the zeolite precursor gel with steam. In other embodiments, the crystallization comprises contacting the zeolite precursor gel with steam at a temperature greater than or equal to 150° C.

In one or more embodiments, the crystalline zeolite intermediate is calcined to produce the mesoporous zeolite. Calcining may remove the mesopores template, leaving behind mesopores in the voids created by the nanocellulosic material. In embodiments, the crystalline zeolite intermediate is calcined by exposure to a temperature of at least 500° C. In other embodiments, the crystalline zeolite intermediate is calcined by exposure to a temperature of at least 550° C.

Without being bound by any particular theory, mesoporous zeolites can be synthesized using hard templates such as nanocellulose-based materials. Mesoporosity may be introduced to zeolites through destructive or constructive methods. Destructive methods include dealumination and desilication, which leach atoms from commercially available materials. However, destructive methods lack control of pore generation, may cause amorphization, have limited flexibility in the Si/Al ratio. Constructive methods involve synthesizing zeolites by crystallizing the mineral around a hard template structure that is burned off during a calcination step, leaving behind pores and channels and are the focus of this disclosure.

In some embodiments, the present disclosure relates to use of hard templates to synthesize mesoporous zeolites. Specifically, embodiments relate to using a nanocellulose mesopore template, such as cellulose nanocrystals (CNC) or cellulose nanofibers (CNF) as hard templates. CNCs are well-defined, highly crystalline nano-sized cellulosic particles that are rod-like and stiff. Cellulose nanocrystals may be formed by treating cellulose (such as from woodpulp) with sulfuric acid to hydrolyze the amorphous regions. The CNCs may have a narrow size distribution, low viscosity and yield strength, as compared to nanocellulose fibers. CNFs are nano-sized cellulose fibrils with a high aspect, or length to width ratio. CNFs are pseudo-plastic with thioxtropy characteristics, meaning they may be viscous and gel-like under normal conditions, but may become less viscous and liquid-like under shearing or agitation. The CNFs may have high viscosity and yield stress along with shear thinning and high water holding capacity. The fibers may form an interconnected network structure.

Both CNCs and CNFs can be inexpensive, widely available, and easily chemically functionalized. As used herein, "functionalization" refers to introducing a chemical functional group to the nanocellulose material to impart various properties into the material, such as, for instance, hydrophobicity, hydrophilicity, surface charges, polarity, electrical conductivity, and the like. Any suitable type of nanocellulose mesopores template may be used, for instance, CNC or CNF may be used to tailor various properties in the zeolite produced. For instance, the kind of CNC or CNF used and the amount of CNC or CNF used may tailor the mesopore size, surface area, and pore volume of the zeolite formed.

In some embodiments, functional groups may be introduced on the surface of CNCs to mitigate the phase-separation and aggregation problems previously described. The size of the particles may be determined by the preparation procedure. The surface of CNCs may contain reactive hydroxyl groups, which can be chemically modified in a variety of ways. The functional groups may be introduced to the surface of the CNCs for a variety of applications, including templating the pores of the growing zeolites and anchoring the zeolites to the mesopore-creating nanoparticles to avoid phase-separation and amorphization of the zeolite materials. Without being bound by any particular theory, introducing functional groups to the CNCs and CNFs may change the polarity of the templates. The polarity may be more compatible with the typically-polar environment of the intermediate mixture (which in some embodiments, may be aqueous, if an aqueous dispersion of CNC or CNF is utilized), thus promoting aggregation of the growing zeolite crystals around the nanocellulosic material.

Without being bound by any theory, use of these nanoparticles may help mitigate the potential issues usually associated with hard template-driven zeolite synthesis. Hard templates may offer improved control over the size and shape of the mesopores formed during the zeolite synthesis; however, conventionally, there have been several drawbacks to the existing hard-templating procedures. One of the problems is aggregation of the template particles within the zeolite gel, which results in the formation of uneven mesopore sites throughout zeolite crystals and partial amorphization of the zeolite material. Another issue that traditionally arises is phase separation along the curvature of the template particles, often associated with the low hydrophilicity of conventional templates, such as carbon Black Pearls®, porous carbons, or carbon fibers. Moreover, the high cost of the hard templates has traditionally been a prohibitive factor. CNC and CNF particles have relatively low cost, high ease of manufacturing, high control over the particle size and morphology, and a variety of ways in which the particles may be chemically modified. CNC particles may be prepared from wood pulp or any other cellulose-containing biomass in a simple sequence of steps involving chemical treatment (acid or base, urea) and sonication to yield nanoparticles in a range of sizes (5 nm to 20 nm in diameter, 100 nm to 1 μm long).

In some embodiments, the CNC, CNF, or both, may be in a colloidal suspension. As used herein, a "colloidal suspension" refers to liquid phase having solid material, for example, particles suspended or otherwise dispersed throughout the fluid. In some embodiments, the CNC, CNF, or both, may be suspended in an aqueous fluid, which may be water, such as deionized or distilled water. In some embodiments, the colloidal suspension may be spray-dried, freeze-dried, or used as it was produced. As a non-limiting example, suitable commercial sources of CNCs and CNFs include U.S. Forest Products Laboratory (USA), American Process, Inc. (USA), Blue Goose (Canada), Cellulose Lab (Canada), CelluForce (Canada), and Borregaard (Norway).

In some embodiments, a silicon-containing material, an aluminum-containing material, or both, may be combined with an alkali meal hydroxide and a quaternary amine to form a zeolite precursor solution. The quaternary amine may be utilized as an SDA for the fabrication of the zeolite microstructure. Quaternary ammonium is generally depicted in Chemical Structure #1. The quaternary ammonium cations serve as crystallization centers for the forming zeolite subunits, thus creating the regular system of micropores in the zeolite structure.

Chemical Structure #1

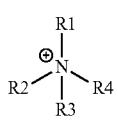

As used throughout this disclosure, the encircled plus symbols ("+") show cationic positively charged centers. R groups (including R1, R2, R3, R4) represent chemical constituents. One or more of the various R groups may be structurally identical or may be structurally different from one another.

In Chemical Structure #1, R1, R2, R3, and R4 may include hydrogen atoms or hydrocarbons, such as a hydrocarbon chain. As used throughout this disclosure, a "hydrocarbon" refers to a chemical or chemical moiety containing only hydrogen and carbon atoms. In some other embodiments, R1, R2, R3, and R4 may contain one or more heteroatoms, such as oxygen, sulfur, nitrogen, or phosphorus. For example, the hydrocarbon chain may be branched or unbranched, and may comprise an alkane hydrocarbon chain, an alkene hydrocarbon chain, or an alkyne hydrocarbon chain, including cyclic or aromatic moieties. In some embodiments, one or more of R1, R2, R3, or R4 may represent hydrogen atoms. As used throughout this disclosure, a heteroatom is a non-carbon and non-hydrogen atom. In embodiments, the quaternary ammonium may be present in a cyclic moiety, such as a five atom ring, a six atom ring, or a ring comprising a different number of atoms. For example, in Chemical Structure #1, the R1 and R2 constituents may be part of the same cyclic moiety.

In one or more embodiments, the two cationic moieties may form ionic bonds with anions. Various anionic chemical species are contemplated, including $Cl^-$, $Br^-$, $F^-$, $I^-$, $OH^-$, ½ $SO_4^{2-}$, ⅓ $PO_4^{3-}$, ½ $S^{2-}$, $AlO_2^-$. In some embodiments, an anion with a negative charge of more than 1-, such as 2-, 3-, or 4-, may be utilized, and in those embodiments, a single anion may pair with multiple cations of the structure-directing agent. As used throughout this disclosure, a fraction listed before an anionic composition means that the anion is paired with more than one cation and may, for example, be paired with the number of cations equal to its negative charge.

In one or more embodiments, two cations of a monomer may be separated from one another by a hydrocarbon chain. The hydrocarbon chain may be branched or unbranched, and may comprise an alkane hydrocarbon chain, an alkene hydrocarbon chain, or an alkyne hydrocarbon chain, including cyclic or aromatic moieties. In one embodiment, the length of the hydrocarbon chain (measured as the number of carbons in the chain directly connecting the two cations) may be from 1 to 10,000 carbon atoms, such 1 to 20 carbon atom alkane chains.

In some embodiments, the quaternary amine may comprise a tetraalkyl ammonium hydroxide, such as tetramethyl ammonium hydroxide (TMAOH). In other embodiments, the quaternary amine may comprise propyltrimethylammonium hydroxide, tetraethylammonium hydroxide, tetrapropylammonium hydroxide, octyltrimethylammonium hydroxide, dodecyltrimethylammonium hydroxide, cetyltrimethylammonium hydroxide, or combinations of these.

A silicon-containing material, an aluminum-containing material, or both, may be mixed with a quaternary amine to produce a zeolite precursor solution. In one or more embodiments, the method further comprises mixing at least one base with the silicon-containing material, the aluminum-containing material, or both, and the quaternary amine. In embodiments, the at least one base comprises sodium hydroxide, potassium hydroxide, lithium hydroxide, and other alkali metal hydroxides, or an alkali earth metal hydroxide. The zeolite precursor solution may be combined with a nanocellulose mesopores template to form a zeolite precursor gel. In one embodiment, the zeolite precursor gel may still contain the cellulosic material, which may at least partially define the space of the mesopores following their removal. The products may be centrifuged, washed, and dried, and finally, the cellulosic material may be removed by a calcination step. The calcination step may comprise exposing the crystalline zeolite intermediate to a temperature of at least 500° C. Without being bound by theory, it is believed that the removal of the cellulosic material forms at least a portion of mesopores of the mesoporous zeolite, where the mesopores are present in the space or voids once inhabited by the cellulosic material.

The zeolite precursor gel, in some embodiments, may be heated under vacuum, such as from a temperature of from 20° C. to 100° C. and at a pressure less than 760 mm Hg. The zeolite precursor gel may undergo nucleation, which may occur as an intermediate material is being heated under vacuum over a period of 1-3 hours at 40 to 80° C. The zeolite precursor gel may then be crystallized using steam to produce a crystalline zeolite intermediate. In some embodiments, crystallization may utilize steam-assisted crystallization of dry gel (SAC-DG) methodology.

In some embodiments, the crystalline zeolite intermediate may be calcined. Calcining may occur in the presence of air at temperatures above 500° C., above 550° C., above 600° C., or even above 750° C. The calcining step may remove the nanocellulose template and structure-directing agents, for instance, by burning them off. Upon calcination, the nanocellulose materials may be removed to give rise to the mesopore-sized voids in the produced mesoporous zeolite. Various heater units are envisioned as suitable, including ovens and autoclaves, or use of any other known techniques in the industry.

In embodiments, the mesoporous zeolites fabricated by the use of the CNC or CNF as hard templates may be characterized as exhibiting a Y or faujasite framework, an MFI (mordenite framework inverted) framework, or a BEA (Beta polymorphs A and B) framework. For example, the mesoporous zeolites described may be characterized as ZSM-5 (that is, having an aluminosilicate MFI framework type), as TS-1 (that is, having a titanosilicate MFI framework type), or as silicalite-I (that is, having a pure silicate MFI framework type) zeolite. In other embodiments, the mesoporous zeolites described may be characterized as Beta (that is, having an aluminosilicate BEA framework type) or faujasite (having a Y-type framework). In some particular embodiments, the mesoporous zeolites fabricated by the methods of the present disclosure may Beta framework zeolites.

Without being bound by any particular theory, the materials of the at least one silicon-containing material, aluminum-containing material, or both, may determine the material composition of the mesoporous zeolite produced, which may be an aluminosilicate, a titanosilicate, or a pure silicate zeolite. In some embodiments, the mesoporous zeolite of the present disclosure may be an aluminosilicate mesoporous zeolite with a molar ratio of Si/Al of greater than or equal to 5, greater than or equal to 10, greater than or equal to 30, or greater than or equal to 50. In some embodiments, the mesoporous zeolite of the present disclosure may be an aluminosilicate mesoporous zeolite with a molar ratio of Si/Al of greater than or equal to 5 and less than 100, greater than or equal to 10 and less than 100, greater than or equal to 25 and less than 100, greater than or equal to 30 and less than 100, greater than or equal to 20 and less than 80, greater than or equal to 40 and less than 80, greater than or equal to 25 and less than 75, or even greater than or equal to 35 and less than 95. In other embodiments, the mesoporous zeolite of the present disclosure may be a pure silicate zeolite, and may have a negligible amount or no amount of aluminum is present, with a Si/Al molar ratio that theoretically approaches infinity. As used herein a "pure silicate" refers to a material comprising at least about 99.9 weight percent (wt. %) of silicon and oxygen atoms. A pure silica mesoporous zeolite may be formed by utilizing only silicon-containing materials and no aluminum.

The mesoporous zeolites of the present disclosure may comprise mesopores and micropores. The mesoporous zeolites may have surface areas and pore volumes greater than that of conventionally produced zeolites. In this disclosure, a "conventional zeolite" or "conventionally produced zeolite" refers to a zeolite that does not substantially comprise mesopores (for example, less than 0.5% of the zeolite pore volume is characterized as mesopores). Without being bound by any particular theory, it is believed that the quaternary amines utilized by the present disclosure may aid in forming the micropores, whereas the mesopores may be formed from the voids created during calcination of the nanocellulose material.

In some embodiments, the mesoporous zeolites of the present disclosure may have an average mesopore size greater than 3 nm, greater than or equal to 10 nm, or greater than or equal to 15 nm. In some embodiments, the average mesopore size may be from 4 nm to 16 nm, from 6 nm to 14 nm, from 8 nm to 12 nm or from 9 nm to 11 nm. In some embodiments, the majority of the mesopores of the mesoporous zeolites of the present disclosure may be greater than 8 nm, greater than 9 nm, or even greater than 10 nm, and may range from 2 nm to 40 nm, with a median pore size of from 6 to 20 nm. Without being bound by theory, it is believed that the mesoporous zeolites of the present disclosure may have enhanced mesoporous characteristics due to the polymer structure of the nanocellulose mesopores template, which when calcined, leaves a plurality of pores in the mesoporous zeolite.

The mesoporous zeolites described in the present disclosure may have enhanced catalytic activity. The high mesoporosity may allow for greater catalytic functionality because more catalytically active sites are available for contact with the reactant in a catalytic reaction. Similarly, the mesopores may allow for better access to microporous catalytic sites on the mesoporous zeolite.

In some embodiments, the mesoporous zeolites may have a surface area of greater than or equal to 300 $cm^2/g$, greater than or equal to 350 $cm^2/g$, greater than or equal to 400 $cm^2/g$, greater than or equal to 450 $cm^2/g$, greater than or equal to 500 $cm^2/g$, greater than or equal to 550 $cm^2/g$, greater than or equal to 600 $cm^2/g$, greater than or equal to 650 $cm^2/g$, or even greater than or equal to 700 $cm^2/g$. The mesoporous zeolites of the present disclosure may have a surface area of from 300 $cm^2/g$ to 1,000 $cm^2/g$, such as from 400 $cm^2/g$ to 800 $cm^2/g$, from 300 $cm^2/g$ to 600 $cm^2/g$, from 350 $cm^2/g$ to 750 $cm^2/g$, from 550 $cm^2/g$ to 1,000 $cm^2/g$, from 550 $cm^2/g$ to 750 $cm^2/g$, or from 650 $cm^2/g$ to 1,000 $cm^2/g$. Having high surface area may allow for increased catalytic activity by increasing the number of chemical reactions that can occur on the catalyst surface.

In one or more other embodiments, the mesoporous zeolites may have a micropore volume of greater than or equal to 0.1 milliliters per gram (mL/g). In some embodiments, the mesoporous zeolites may have a micropore volume of greater than or equal to 0.15 mL/g, or even greater than or equal to 0.2 mL/g. In some embodiments, the mesoporous zeolites may have a mesopore volume of greater than or equal to 0.3 mL/g. The mesoporous zeolites may have a mesopore volume of greater than or equal to 0.35 mL/g, greater than or equal to 0.4 mL/g, greater than or equal to 0.45 mL/g, greater than or equal to 0.5 mL/g, greater than or equal to 0.55 mL/g, greater than or equal to mL/g, greater than or equal to 0.65 mL/g, or even greater than or equal to 0.7 mL/g and less than or equal to 1.5 mL/g.

In further embodiments, the portion of the surface area contributed by mesopores may be greater than or equal to 20%, greater than or equal to 25%, greater than or equal to 30%, greater than or equal to 35%, greater than or equal to 40%, greater than or equal to 45%, greater than or equal to 50%, greater than or equal to 55%, greater than or equal to 60%, or even greater than or equal to 65%, such as between 20% and 70% of total surface area. In additional embodiments, the portion of the pore volume contributed by mesopores may be greater than or equal to 20%, greater than or equal to 30%, greater than or equal to 35%, greater than or equal to 40%, greater than or equal to 45%, greater than or equal to 50%, greater than or equal to 55%, greater than or equal to 60%, greater than or equal to 65%, greater than or equal to 70%, or even greater than or equal to 75%, such as between 20% and 80% of total pore volume. Surface area and pore volume distribution may be measured by Ar adsorption isotherms performed at 87 Kelvin (K) (such as with a Micrometrics ASAP 2020 system).

The mesoporous zeolites described may form as particles that may be generally spherical in shape or irregular globular shaped (that is, non-spherical). In embodiments, the particles have a "particle size" measured as the greatest distance between two points located on a single zeolite particle. For example, the particle size of a spherical particle would be its diameter. In other shapes, the particle size is measured as the distance between the two most distant points of the same particle, where these points may lie on outer surfaces of the particle. The particles may have a particle size from 25 nm to 500 nm, from 50 nm to 400 nm, from 100 nm to 300 nm, or less than 900 nm, less than 800 nm, less than 700 nm, less than 600 nm, less than 500 nm, less than 400 nm, less than 300 nm, or less than 250 nm. Particle sizes may be determined by examination under a TEM or SEM microscope.

Without being bound by any particular theory, the mesoporous zeolites produced may exhibit high surface area and high micropore volume, indicating high crystallinity of the material and intact system micropores. The high crystallinity and intact micropores may increase catalytic activity, resulting in a more effective catalyst. In some embodiments, the mesoporous zeolites may have a crystallinity of at least 90% as measured using x-ray diffraction (XRD), as compared to commercial zeolite material produced. The mesoporous zeolites may have a crystallinity of at least 50%, at least 60%, at least 70%, at least 80%, at least 90%, at least 92%, at least 95%, at least 98%, at least 100%, or at least 105%, as measured using XRD, as compared to commercial zeolite material produced. The relative crystallinity is determined by comparison to the absolute crystallinity of commercially available microporous zeolite, which is assigned as 100% crystalline. Integration of the chosen peaks in the XRD traces allows for direct comparison of the mesoporous materials to the conventionally synthesized microporous zeolite.

Moreover, the mesoporous zeolites produced may have an average pore size of 20 nm, significantly larger than conventional zeolite pore size, as well as high mesopore volumes, allowing for the upgrading of larger molecules. In some embodiments, due to the large pore size, the mesoporous zeolites produced by the methods of the present disclosure may be able to upgrade or "crack" large aromatic molecules, including polycyclic aromatic and heteroaromatic molecules. In some embodiments, the mesoporous zeolites may be able to upgrade conditioned crude oil, such as vacuum residue fractions. In some embodiments, the mesoporous zeolites produced by the methods of the present disclosure may be able to upgrade vacuum residue fractions having boiling points over 550° C., such as fractions having boiling points over 575° C., over, 600° C., over 650° C., or even over 700° C.

EXAMPLES

Using the methods of the present disclosure, mesoporous zeolites were produced to exemplify the attributes previously described. Four example methods were undertaken in accordance with the present disclosure in which the ratio of silica ($SiO_2$) to alumina ($Al_2O_3$) was varied. Another four example methods were conducted varying the amount and type of cellulosic material used.

Example 1—Si/Al Ratio of 15

Example 1 was prepared by suspending 3.45 grams (g) of fumed silica in 80 g of $H_2O$. Then, 0.283 g of NaOH in 5 mL of water followed by 15.23 g of TEAOH (35% aqueous) was both added to the fumed silica. The mixture was stirred vigorously for one hour. In a separate beaker, 1.44 g $Al(NO_3)_3 \cdot 9H_2O$ was dissolved in 50 g $H_2O$ and the resulting solution was added to the suspended fumed silica mixture. The mixture was stirred for 30 minutes. 1.0 g of previously freeze-dried CNC was suspended in approximately 20 mL $H_2O$ and homogenized using an acoustic mixer LabRam at 80% (70 G acceleration) intensity for 1 hour. The resulting opaque suspension was added to the mixture and was stirred for 30 minutes. The volatiles were removed on a rotary evaporator with a bath heated to 60° C. The resulting yellow-white sticky solid was crushed in a mortar. The resulting glass-like gel powder was transferred into a 15 mL crucible placed on top of a Teflon rod in a 125 mL acid digestion bomb. The bomb was charged with 20 mL of water, was sealed, and was heated to 150° C. for 40 hours. The brown solids produced were washed 3 times with 80 mL of water using an ultracentrifuge, and then dried at 60° C. for 18 hours. The off-white solids were calcined at 550° C. for 12 hours. The calcined solids were then suspended in 1M $NH_4Cl$ solution (10 mL per 1 g of zeolite) at 90° C. overnight. The solids were isolated by centrifugation and washed with water 4 times using 50 mL. The ion exchange was repeated twice. The solids were dried overnight at 60° C. and were calcined at 550° C. for 12 hours. FIG. 1A is an XRD of Example 1. As shown in FIG. 1A, Example 1 is crystalline in nature.

Example 2—Si/Al Ratio of 30

Figure 1B:
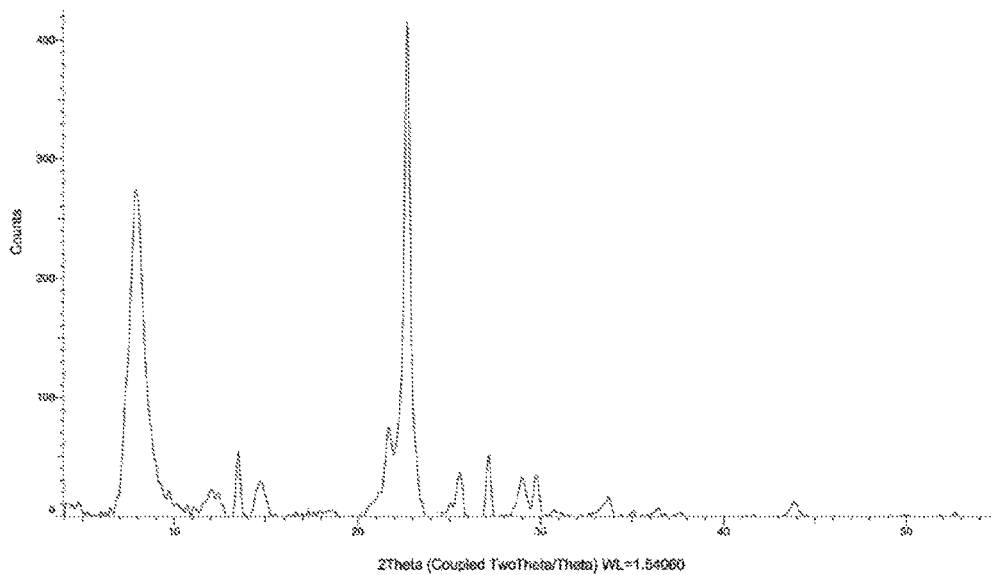
FIG. 1B is an XRD graph of Example 2, according to embodiments shown and described herein.

Example 2 was prepared by suspending 3.45 grams (g) of fumed silica in 80 g of $H_2O$. Then, 0.166 g of NaOH in 5 mL of water and 8.96 g of TEAOH (35% aqueous) were both added to the fumed silica. The mixture was stirred vigorously for one hour. In a separate beaker, 0.720 g $Al(NO_3)_3 \cdot 9H_2O$ was dissolved in 20 g $H_2O$ and the resulting solution was added to the suspended fumed silica mixture. The mixture was stirred for 30 minutes. 0.75 of previously freeze-dried CNC was suspended in approximately 20 mL $H_2O$ and homogenized using an acoustic mixer LabRam at 80% (70 G acceleration) intensity for 1 hour. The resulting opaque suspension was added to the mixture and was stirred for 30 minutes. The volatiles were removed on a rotary evaporator with a bath heated to 60° C. The resulting yellow-white sticky solid was crushed in a mortar. The resulting glass-like gel powder was transferred into a 15 mL crucible placed on top of a Teflon rod in a 125 mL acid digestion bomb. The bomb was charged with 20 mL of water, was sealed, and was heated to 150° C. for 40 hours. The brown solids produced were washed 3 times with 80 mL of water using an ultracentrifuge, and then dried at 60° C. for 18 hours. The off-white solids were calcined at 550° C. for 12 hours. The calcined solids were then suspended in 1M $NH_4Cl$ solution (10 mL per 1 g of zeolite) at 90° C. overnight. The solids were isolated by centrifugation and washed with water 4 times using 50 mL. The ion exchange was repeated twice. The solids were dried overnight at 60° C. and were calcined at 550° C. for 12 hours. FIG. 1B is an XRD of Example 2. As shown in FIG. 1B, Example 2 is crystalline in nature.

Example 3—Si/Al Ratio of 50

Figure 2A:
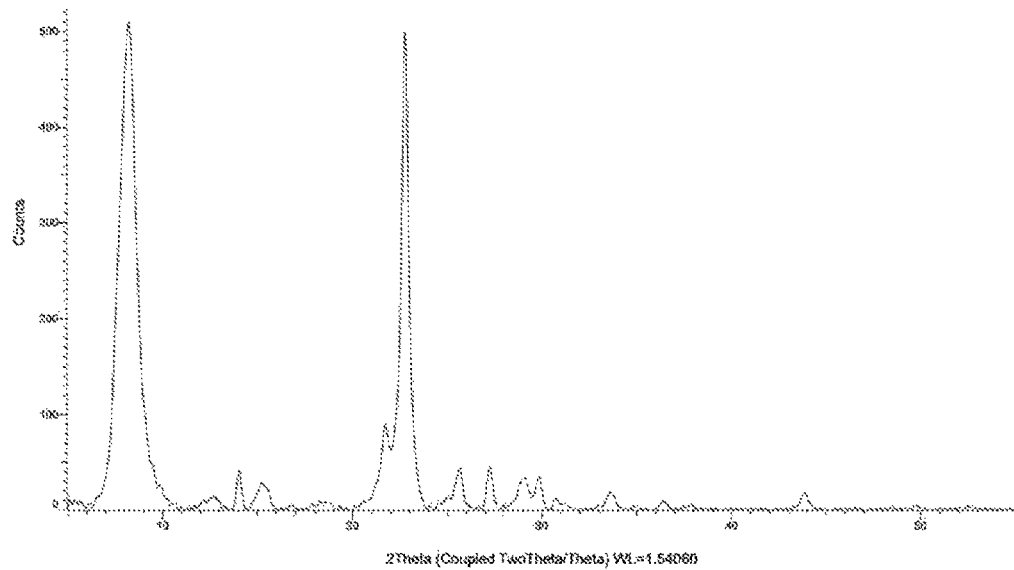
FIG. 2A is an XRD graph of Example 3, according to embodiments shown and described herein.

Example 3 was prepared in accordance with the method described in Example 2, except 0.430 g $Al(NO_3)_3 \cdot 9H_2O$ was dissolved in 20 g $H_2O$. FIG. 2A is an XRD of Example 3. As shown in FIG. 2A Example 3 was also crystalline in nature.

Example 4—Si/Al Ratio of 70

Figure 2B:
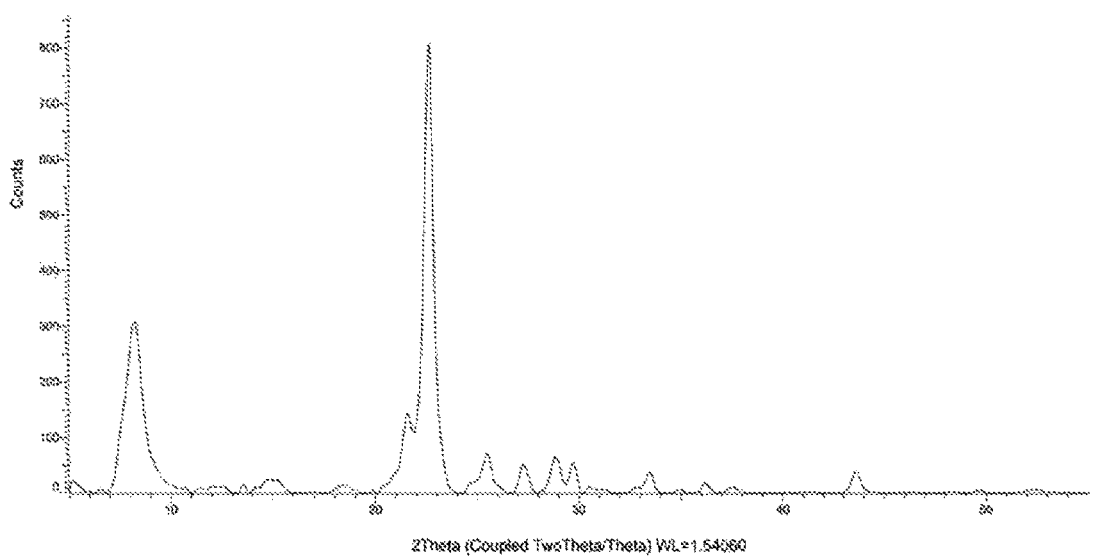
FIG. 2B is an XRD graph of Example 4, according to embodiments shown and described herein.

Example 4 was prepared in accordance with the method described in Example 2, except 0.310 g $Al(NO_3)_3 \cdot 9H_2O$ was dissolved in 20 g $H_2O$. FIG. 2B is an XRD of Example 4. As shown in FIG. 2B, Example 4 was also crystalline in nature.

The properties of Examples 1-4 are listed in Table 1. As previously described, the mesoporous zeolites produced by the methods of the present disclosure exhibit high surface area and high micropore volume, indicating high crystallinity of the material and intact system micropores. The high crystallinity and intact micropores may increase catalytic activity, resulting in a more effective catalyst. Moreover, the mesoporous zeolites produced may have an average pore size of 20 nm, significantly larger than conventional zeolite pore size, as well as high mesopore volumes, allowing for the upgrading of larger molecules.

TABLE 1

Examples 1-4 with Varying Si/Al Ratios

| Property | Example 1 Si/Al = 15 | Example 2 Si/Al = 30 | Example 3 Si/Al = 50 | Example 4 Si/Al = 70 |
|---|---|---|---|---|
| BET Surface Area ($m^2/g$) | 622.9 | 581.2 | 714.5 | 595.2 |
| t-Plot Micropore Area ($m^2/g$) | 500.0 | 398.5 | 563.7 | 426.8 |
| t-Plot External Surface Area ($m^2/g$) | 122.9 | 182.71 | 151.2 | 168.3 |
| t-Plot Micropore Volume ($cm^3/g$) | 0.222 | 0.205 | 0.280 | 0.171 |
| BJH Adsorption cumulative surface area of pores between 17 Å and 3,000 Å diameter ($m^2/g$) | 99.8 | 153.1 | 117.5 | 152.1 |
| BJH Adsorption cumulative volume of pores between 17 Å and 3,000 Å diameter ($cm^3/g$) | 0.291 | 0.643 | 0.331 | 0.600 |
| BJH Adsorption average pore diameter (4 V/A)(Å) | 136.3 | 209.6 | 114.8 | 157.8 |

Additional examples were tested using various forms of cellulosic material. One example, Example 5, contained freeze-dried CNCs suspended in water that were subjected to LabRam ResonantAcoustic® Mixer. Another example, Example 6, utilized a commercial suspension of CNC diluted with water that was used as-is. Example 7 was a scaled-up synthesis with a Si/Al ratio of 30 and 10% CNC loading. Finally, Example 8 utilized CNFs as the hard template.

Example 5—Freeze-Dried CNC

Figure 3A:
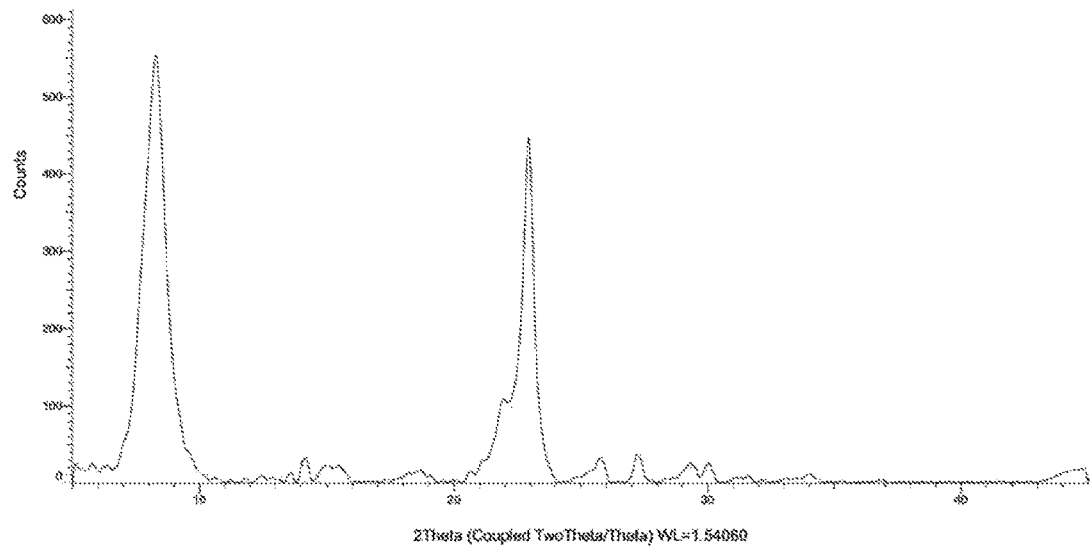
FIG. 3A is an XRD graph of Example 5, according to embodiments shown and described herein.

Example 5 was prepared by suspending 3.45 g of fumed silica in 80 g of $H_2O$. Then, 0.166 g of NaOH in 5 mL of water and 8.96 g of TEAOH (35% aqueous) were both added to the fumed silica. The mixture was stirred vigorously for one hour. In a separate beaker, 0.720 g $Al(NO_3)_3 \cdot 9H_2O$ was dissolved in 20 g $H_2O$ and the resulting solution was added to the suspended fumed silica mixture. The mixture was stirred for 30 minutes. 0.75 g of previously freeze-dried CNC was suspended in approximately 20 mL $H_2O$ and homogenized using an acoustic mixer LabRam at 80% (70 G acceleration) intensity for 1 hour. The resulting opaque suspension was added to the mixture and was stirred for 30 minutes. The volatiles were removed on a rotary evaporator with a bath heated to 60° C. The resulting yellow-white sticky solid was crushed in a mortar. The resulting glass-like gel powder was transferred into a 15 mL crucible placed on top of a Teflon rod in a 125 mL acid digestion bomb. The bomb was charged with 20 mL of water, was sealed, and was heated to 150° C. for 40 hours. The brown solids produced were washed 3 times with 80 mL of water using an ultracentrifuge, and then dried at 60° C. for 18 hours. The off-white solids were calcined at 550° C. for 12 hours. The calcined solids were then suspended in 1M $NH_4Cl$ solution (10 mL per 1 g of zeolite) at 90° C. overnight. The solids were isolated by centrifugation and washed with water 4 times using 50 mL. The ion exchange was repeated twice. The solids were dried overnight at 60° C. and were calcined at 550° C. for 12 hours. FIG. 3A is an XRD of Example 5. As shown in FIG. 3A, Example 5 is crystalline in nature.

Example 6—Commercial Suspension of CNC

Figure 3B:
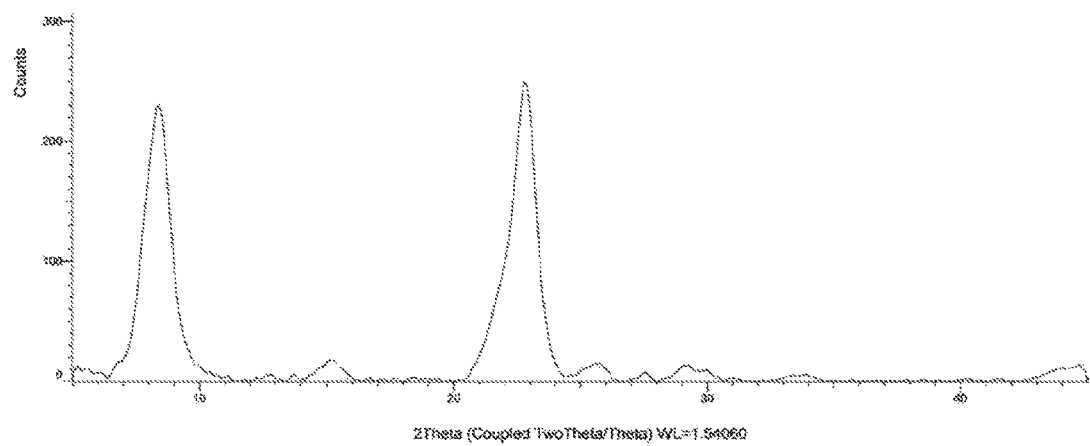
FIG. 3B is an XRD graph of Example 6, according to embodiments shown and described herein.

Example 6 was prepared by suspending 3.45 g of fumed silica in 80 g of $H_2O$. Then, 0.166 g of NaOH in 5 mL of water and 8.96 g of TEAOH (35% aqueous) were both added to the fumed silica. The mixture was stirred vigorously for one hour. In a separate beaker, 0.720 g $Al(NO_3)_3 \cdot 9H_2O$ was dissolved in 20 g $H_2O$ and the resulting solution was added to the suspended fumed silica mixture. The mixture was stirred for 30 minutes. 6.8 g (0.75 g CNC in an 11% suspension) of the commercially supplied CNC (U.S Forest Product Laboratory, cellulose nanocrystals 5-20 nm wide, 150-200 nm long) was diluted with 10 mL water and stirred vigorously for 20 minutes. The resulting opaque suspension was added to the mixture and was stirred for 30 minutes. The volatiles were removed on a rotary evaporator with a bath heated to 60° C. The resulting yellow-white sticky solid was crushed in a mortar. The resulting glass-like gel powder was transferred into a 15 mL crucible placed on top of a Teflon rod in a 125 mL acid digestion bomb. The bomb was charged with 20 mL of water, was sealed, and was heated to 150° C. for 40 hours. The brown solids produced were washed 3 times with 80 mL of water using an ultracentrifuge, and then dried at 60° C. for 18 hours. The off-white solids were calcined at 550° C. for 12 hours. The calcined solids were then suspended in a 1M $NH_4Cl$ solution (10 mL per 1 g of zeolite) at 90° C. overnight. The solids were isolated by centrifugation and washed with water 4 times using 50 mL. The ion exchange was repeated twice. The solids were dried overnight at 60° C. and were calcined at 550° C. for 12 hours. FIG. 3B is an XRD of Example 6. As shown in FIG. 3B, Example 6 is crystalline in nature.

Example 7—Scaled Synthesis

Figure 4A:
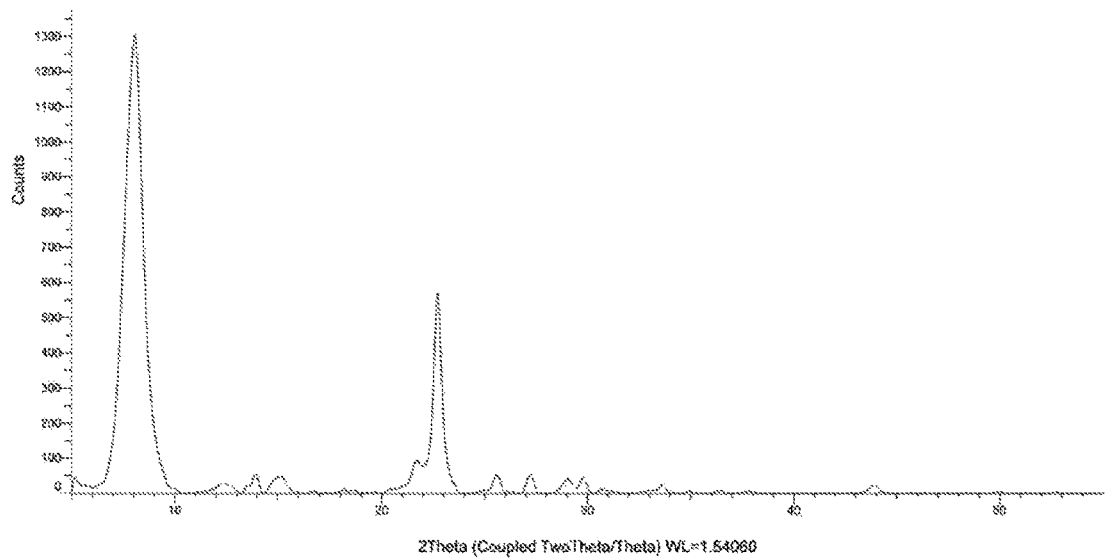
FIG. 4A is an XRD graph of Example 7, according to embodiments shown and described herein.

Example 7 was prepared by suspending 34.5 g of fumed silica in 600 g of $H_2O$. Then, 1.66 g of NaOH in 25 mL of water followed by 89.6 g of TEAOH (35% aqueous) were both added to the fumed silica. The mixture was stirred vigorously for one hour. In a separate beaker, 4.3 g $Al(NO_3)_3 \cdot 9H_2O$ was dissolved in 20 g $H_2O$ and the resulting solution was added to the suspended fumed silica mixture. The mixture was stirred for 30 minutes. 7.5 g CNC was suspended in 150 g $H_2O$ and homogenized using acoustic sonicator LabRam at 50% (56 G acceleration) intensity for 15 minutes. The suspension was added to the mixture and was stirred for 30 minutes. The volatiles were removed on a rotary evaporator with a bath heated to 60° C. The resulting yellow-white sticky solid was crushed in a mortar. The resulting glass-like gel powder was transferred into a 100 mL Teflon dish and placed on top of a Teflon rod in a 1 L acid digestion bomb. The bomb was charged with 120 mL of water, was sealed, and was heated to 150° C. for 48 hours. The brown solids produced were washed 3 times with 150 mL of water using an ultracentrifuge, and then dried at 60° C. overnight. The off-white solids were calcined at 550° C. for 8 hours using a 1° C./min. ramp. The calcined solids were then suspended in a 1M $NH_4Cl$ solution (10 mL per 1 g of zeolite) at 90° C. overnight. The solids were isolated by centrifugation and washed with water 2 times using 150 mL. The exchange was repeated twice. The solids were dried overnight at 60° C. and were calcined at 550° C. for 5 hours using a 1° C./min. ramp. FIG. 4A is an XRD of Example 7. As shown in FIG. 4A, Example 7 is crystalline in nature.

Example 8—CNF

Figure 4B:
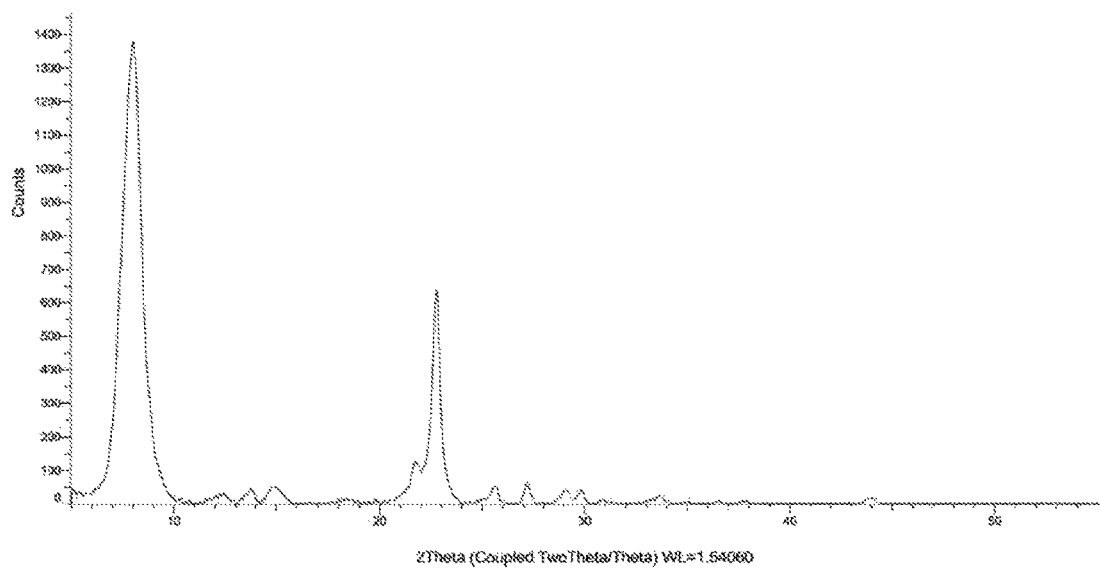
FIG. 4B is an XRD graph of Example 8, according to embodiments shown and described herein.

Finally, Example 8 was prepared by suspending 3.45 g of fumed silica in 80 g of $H_2O$. Then, 0.166 g of NaOH in 5 mL of water and 8.96 g of TEAOH (35% aqueous) were both added to the fumed silica. The mixture was stirred vigorously for one hour. In a separate beaker, 0.720 g Al$(NO_3)_3 \cdot 9H_2O$ was dissolved in 20 g $H_2O$ and the resulting solution was added to the suspended fumed silica mixture. The mixture was stirred for 30 minutes. 0.75 g CNF was suspended in $H_2O$ and 26.8 g of the suspension was added to the mixture and stirred vigorously for 30 minutes. The volatiles were removed on a rotary evaporator with a bath heated to 60° C. The resulting yellow-white sticky solid was crushed in a mortar. The resulting glass-like gel powder was transferred into a 15 mL Teflon beaker and placed on top of a Teflon rod in a 125 mL acid digestion bomb. The bomb was charged with 20 mL of water, was sealed, and was heated to 150° C. for 40 hours. The brown solids produced were washed 3 times with 80 mL of water using an ultracentrifuge, and then dried at 60° C. for 18 hours. The off-white solids were calcined at 550° C. for 12 hours. The calcined solids were then suspended in 1M $NH_4Cl$ solution (10 mL per 1 g of zeolite) at 90° C. overnight. The solids were isolated by centrifugation. The ion exchange was repeated twice. The solids were dried overnight at 60° C. and were calcined at 550° C. for 12 hours. FIG. 4B is an XRD of Example 8. As shown in FIG. 4B, Example 8 is crystalline in nature.

The properties of Examples 5-8 are listed in Table 2.

TABLE 2

Examples 5-8 with Varying Cellulosic Material

| Property | Example 5 Freeze-dried CNC | Example 6 Commercial CNC | Example 7 Large Scale CNC | Example 8 CNF |
|---|---|---|---|---|
| BET Surface Area (m²/g) | 634.9 | 220.6 | 764.0 | 720.2 |
| t-Plot Micropore Area (m²/g) | 523.4 | 132.2 | 613.2 | 591.4 |
| t-Plot External Surface Area (m²/g) | 111.4 | 88.4 | 150.8 | 128.8 |
| t-Plot Micropore Volume (cm³/g) | 0.204 | 0.049 | 0.223 | 0.216 |
| BJH Adsorption cumulative surface area of pores between 17 Å and 3,000 Å diameter (m²/g) | 85.4 | 74.0 | 122.0 | 123.4 |
| BJH Adsorption cumulative volume of pores between 17 Å and 3,000 Å diameter (cm³/g) | 0.445 | 0.435 | 0.484 | 0.374 |
| BJH Adsorption average pore diameter (4 V/A)(Å) | 208.4 | 233.7 | 158.6 | 121.4 |

Example 9—Si/Al Ratio of 30; 5 wt. % Freeze-Dried CNC

Figure 5A:
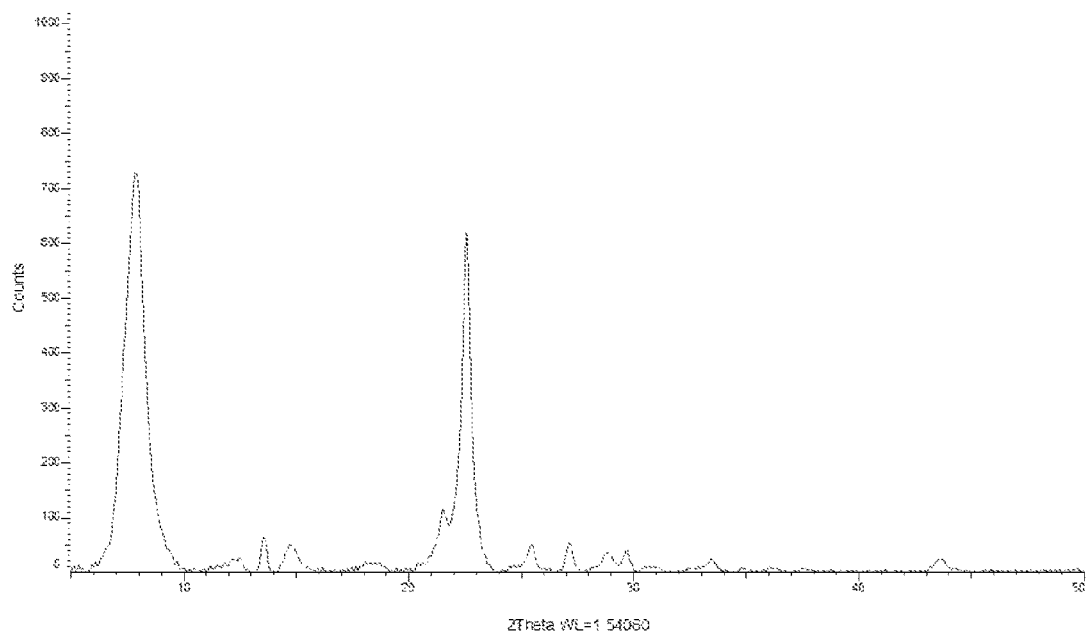
FIG. 5A is an XRD graph of Example 9, according to embodiments shown and described herein.

Example 9 was prepared by first suspending 5.0 g of fumed silica in 80 g of $H_2O$. Then, 0.241 g of NaOH in 5 ml of $H_2O$ followed by 13.0 g of TEAOH (35% aqueous) were both added to the fumed silica. The mixture was stirred vigorously for 30 minutes. In a separate beaker, 1.04 g of Al$(NO_3)_3 \cdot 9H_2O$ was dissolved in 5 g of $H_2O$ and the resulting solution was added to the suspended fumed silica mixture. The mixture was stirred for 30 minutes. 570 mg of CNC were suspended in 10 g of $H_2O$ and homogenized using LabRam at 50% intensity (56 G acceleration) for 5 min. The suspension was added to the mixture and stirred for 90 minutes. The volatiles were removed on a rotary evaporator with a bath heated to 60° C. The resulting glass-like gel powder was transferred into a 25 ml PTFE beaker and placed on top of a Teflon rod into a 125 mL acid digestion bomb. The bomb was charged with 20 ml of water, sealed, and heated to 150° C. for 40 hours. The brown solids were washed with water (3 rinses using 80 mL each) using an ultracentrifuge, then dried at 100° C. for 7 h. The off-white solids were calcined at 550° C. for 8 h. The calcined solids were suspended in 1M $NH_4Cl$ solution (at a ratio of 10 ml of $NH_4Cl$ to 1 g of zeolite) at 90° C. overnight. The solids were isolated by centrifugation and the exchange was repeated twice. The solids were washed with water (4 rinses using 80 mL each) and dried at 60° C. overnight. Finally, the solids were calcined at 550° C. for 6 h. FIG. 5A is an XRD of Example 9.

Example 10—Si/Al Ratio of 30; 5 wt. % Commercial CNC

Figure 5B:
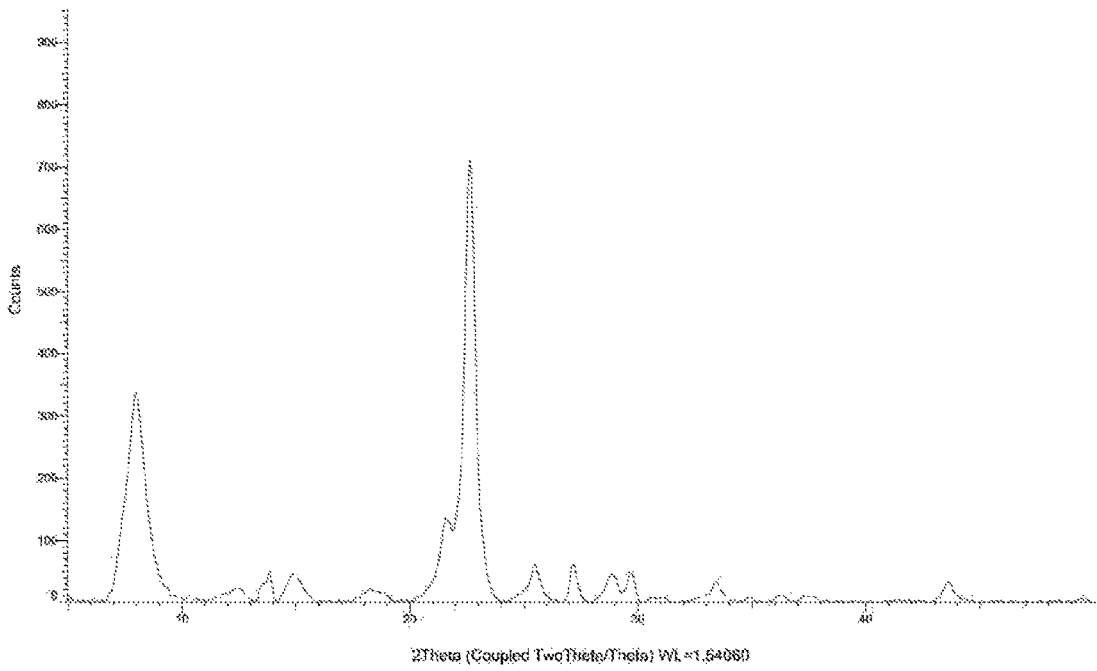
FIG. 5B is an XRD graph of Example 10, according to embodiments shown and described herein.

Example 10 was prepared by first suspending 5.0 g of fumed silica in 80 g of $H_2O$. Then, 0.241 g of NaOH in 5 ml of $H_2O$ followed by 13.0 g of TEAOH (35% aqueous) were both added to the fumed silica. The mixture was stirred vigorously for 30 minutes. In a separate beaker, 1.04 g of Al$(NO_3)_3 \cdot 9H_2O$ was dissolved in 5 g of $H_2O$ and the resulting solution was added to the suspended fumed silica mixture. The mixture was stirred for 30 minutes. Then, 5.18 g of a commercially available 11% aqueous CNC suspension were added to the mixture. The mixture was then stirred for 90 minutes. The volatiles were removed on a rotary evaporator with a bath heated to 60° C. The resulting glass-like gel powder was transferred into a 25 ml PTFE beaker and placed on top of a Teflon rod into a 125 mL acid digestion bomb. The bomb was charged with 20 ml of water, sealed, and heated to 150° C. for 40 hours. The brown solids were washed with water (3 rinses using 80 mL each) using an ultracentrifuge, then dried at 100° C. for 7 h. The off-white solids were calcined at 550° C. for 8 h. The calcined solids were suspended in 1M $NH_4Cl$ solution (at a ratio of 10 ml of $NH_4Cl$ to 1 g of zeolite) at 90° C. overnight. The solids were isolated by centrifugation and the exchange was repeated twice. The solids were washed with water (4 rinses using 80 mL each) and dried at 60° C. overnight. Finally, the solids were calcined at 550° C. for 6 h. FIG. 5B is an XRD of Example 10.

Example 11—Si/Al Ratio of 30; 10 wt. % Freeze-Dried CNC

Figure 6A:
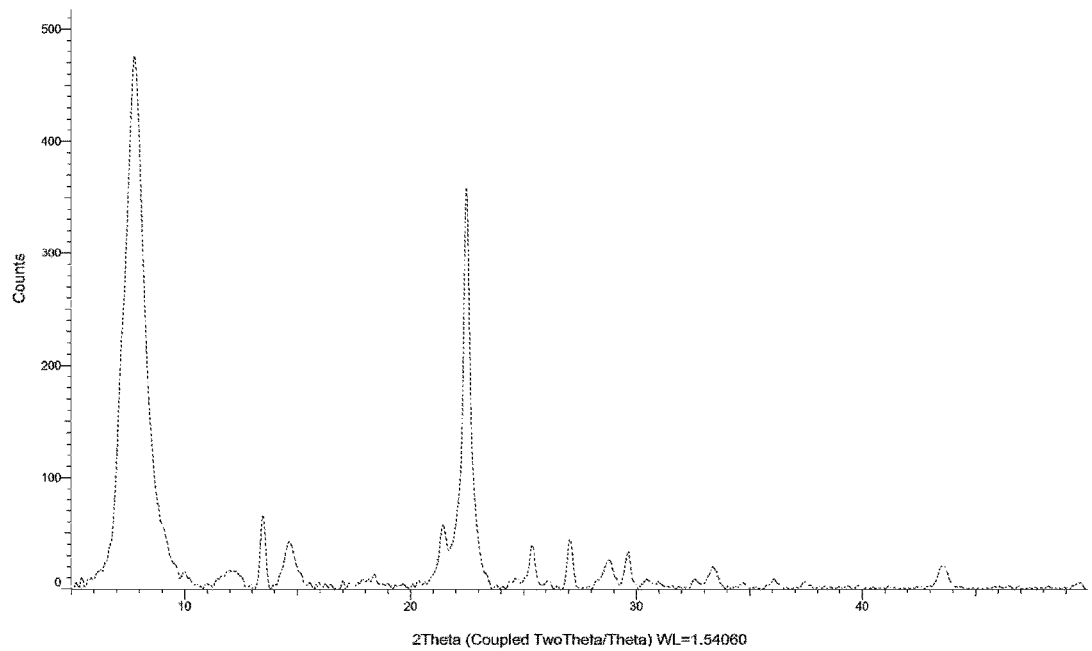
FIG. 6A is an XRD graph of Example 11, according to embodiments shown and described herein.

Example 11 was prepared by first suspending 5.0 g of fumed silica in 80 g of $H_2O$. Then, 0.241 g of NaOH in 5 ml of $H_2O$ followed by 13.0 g of TEAOH (35% aqueous) were both added to the fumed silica. The mixture was stirred vigorously for 30 minutes. In a separate beaker, 1.04 g of $Al(NO_3)_3 \cdot 9H_2O$ was dissolved in 5 g of $H_2O$ and the resulting solution was added to the suspended fumed silica mixture. The mixture was stirred for 30 minutes. 1.2 g of CNC was suspended in 10 g of $H_2O$ and homogenized using LabRam at 50% intensity (56 G acceleration) for 5 min. The suspension was added to the mixture and stirred for 90 minutes. The volatiles were removed on a rotary evaporator with a bath heated to 60° C. The resulting glass-like gel powder was transferred into a 25 ml PTFE beaker and placed on top of a Teflon rod into a 125 mL acid digestion bomb. The bomb was charged with 20 ml of water, sealed, and heated to 150° C. for 40 hours. The brown solids were washed with water (3 rinses using 80 mL each) using an ultracentrifuge, then dried at 100° C. for 7 h. The off-white solids were calcined at 550° C. for 8 h. The calcined solids were suspended in 1M $NH_4Cl$ solution (at a ratio of 10 ml of $NH_4Cl$ to 1 g of zeolite) at 90° C. overnight. The solids were isolated by centrifugation and the exchange was repeated twice. The solids were washed with water (4 rinses using 80 mL each) and dried at 60° C. overnight. Finally, the solids were calcined at 550° C. for 6 h. FIG. 6A is an XRD of Example 11.

Example 12—Si/Al Ratio of 30; 10 wt. % Commercial CNC

Figure 6B:
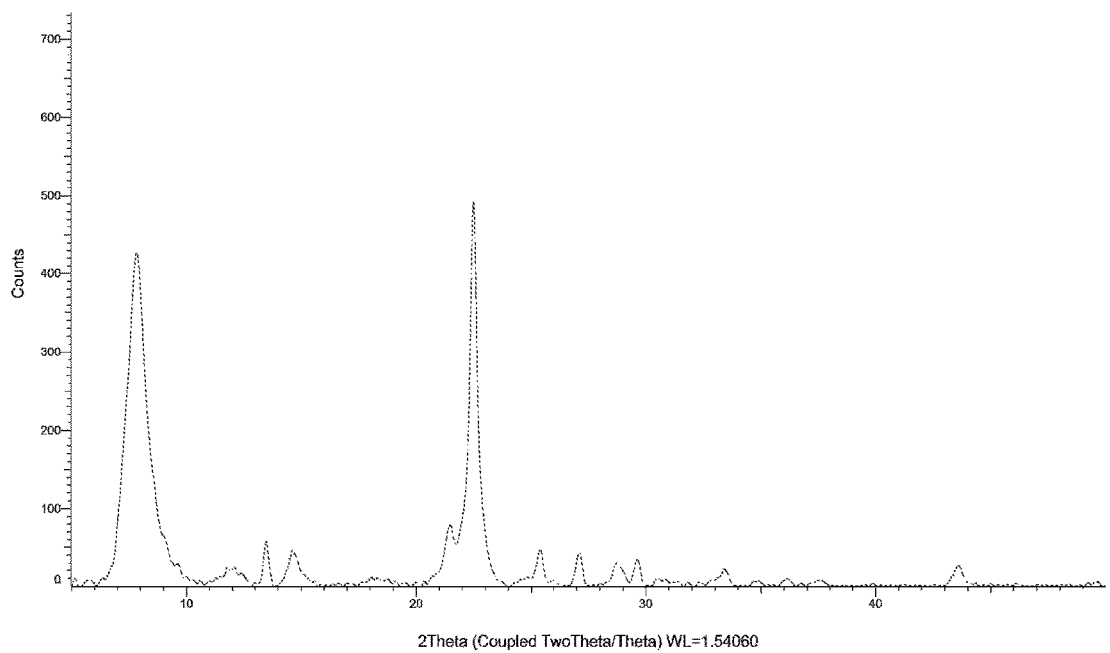
FIG. 6B is an XRD graph of Example 12, according to embodiments shown and described herein.

Example 12 was prepared by first suspending 5.0 g of fumed silica in 80 g of $H_2O$. Then, 0.241 g of NaOH in 5 ml of $H_2O$ followed by 13.0 g of TEAOH (35% aqueous) were both added to the fumed silica. The mixture was stirred vigorously for 30 minutes. In a separate beaker, 1.04 g of $Al(NO_3)_3 \cdot 9H_2O$ was dissolved in 5 g of $H_2O$ and the resulting solution was added to the suspended fumed silica mixture. The mixture was stirred for 30 minutes. Then, 10.9 g of a commercially available 11% aqueous CNC suspension were added to the mixture. The mixture was then stirred for 90 minutes. The volatiles were removed on a rotary evaporator with a bath heated to 60° C. The resulting glass-like gel powder was transferred into a 25 ml PTFE beaker and placed on top of a Teflon rod into a 125 mL acid digestion bomb. The bomb was charged with 20 ml of water, sealed, and heated to 150° C. for 40 hours. The brown solids were washed with water (3 rinses using 80 mL each) using an ultracentrifuge, then dried at 100° C. for 7 h. The off-white solids were calcined at 550° C. for 8 h. The calcined solids were suspended in 1M $NH_4Cl$ solution (at a ratio of 10 ml of $NH_4Cl$ to 1 g of zeolite) at 90° C. overnight. The solids were isolated by centrifugation and the exchange was repeated twice. The solids were washed with water (4 rinses using 80 mL each) and dried at 60° C. overnight. Finally, the solids were calcined at 550° C. for 6 h. FIG. 6B is an XRD of Example 12.

Example 13—Si/Al Ratio of 60; 10 wt. % Freeze-Dried CNC

Figure 7A:
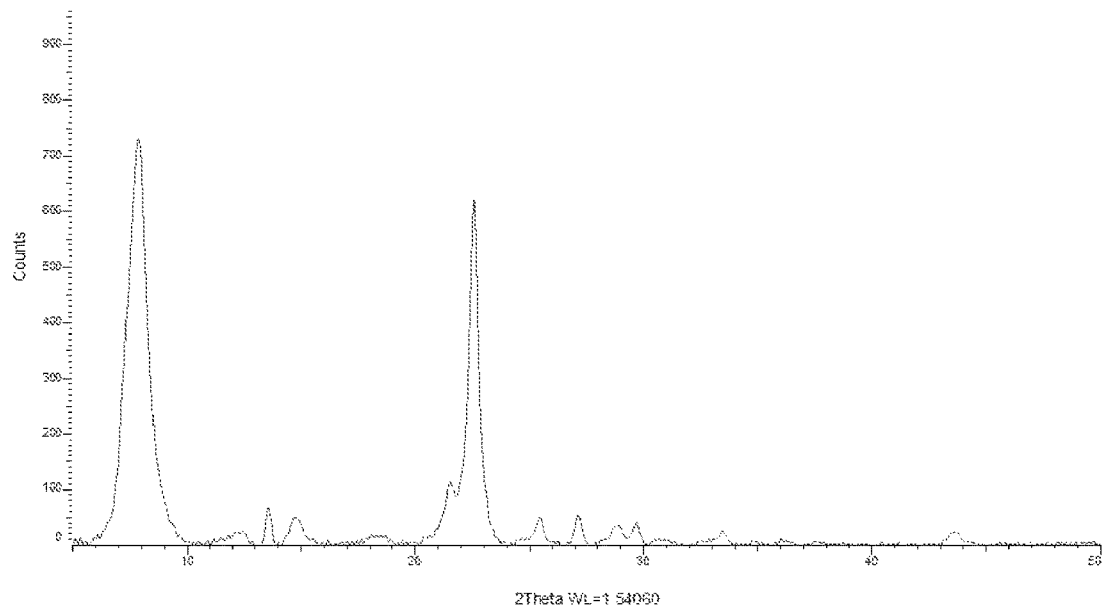
FIG. 7A is an XRD graph of Example 13, according to embodiments shown and described herein.

Example 13 was prepared by first suspending 5.0 g of fumed silica in 80 g of $H_2O$. Then, 0.241 g of NaOH in 5 ml of $H_2O$ followed by 13.0 g of TEAOH (35% aqueous) were both added to the fumed silica. The mixture was stirred vigorously for 30 minutes. In a separate beaker, 1.04 g of $Al(NO_3)_3 \cdot 9H_2O$ was dissolved in 5 g of $H_2O$ and the resulting solution was added to the suspended fumed silica mixture. The mixture was stirred for 30 minutes. Then, 980 mg of CNC was suspended in 10 g of $H_2O$ and homogenized using LabRam at 50% intensity (56 G acceleration) for 5 min. The suspension was added to the mixture and stirred for 90 minutes. The volatiles were removed on a rotary evaporator with a bath heated to 60° C. The resulting glass-like gel powder was transferred into a 25 ml PTFE beaker and placed on top of a Teflon rod into a 125 mL acid digestion bomb. The bomb was charged with 20 ml of water, sealed, and heated to 150° C. for 40 hours. The brown solids were washed with water (3 rinses using 80 mL each) using an ultracentrifuge, then dried at 100° C. for 7 h. The off-white solids were calcined at 550° C. for 8 h. The calcined solids were suspended in 1M $NH_4Cl$ solution (at a ratio of 10 ml of $NH_4Cl$ to 1 g of zeolite) at 90° C. overnight. The solids were isolated by centrifugation and the exchange was repeated twice. The solids were washed with water (4 rinses using 80 mL each) and dried at 60° C. overnight. Finally, the solids were calcined at 550° C. for 6 h. FIG. 7A is an XRD of Example 13.

Example 14—Si/Al Ratio of 30; 2.5 wt. % Freeze-Dried CNC

Figure 7B:
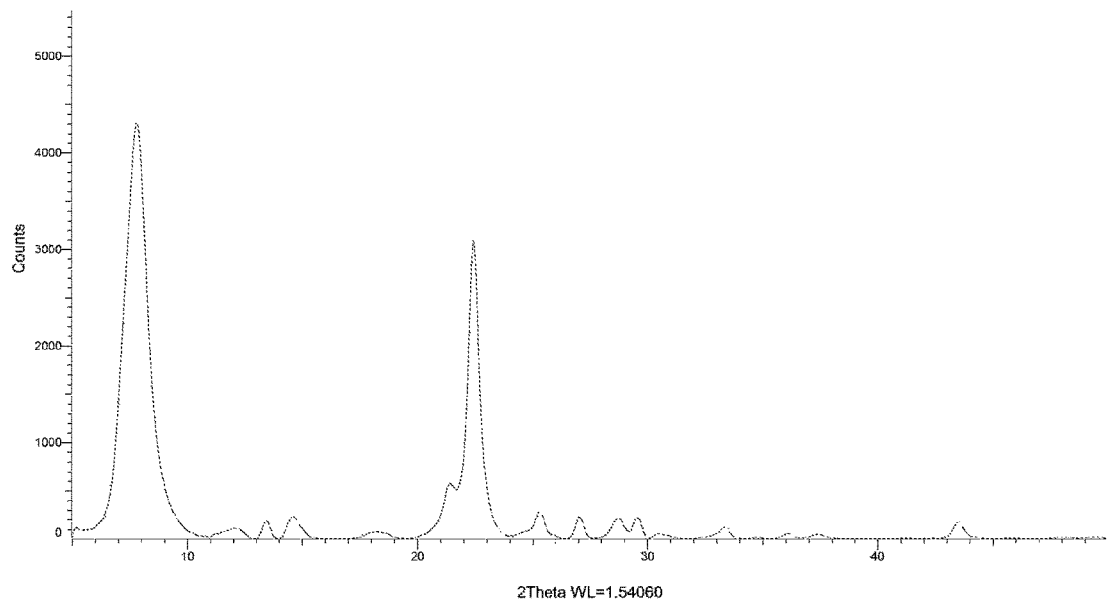
FIG. 7B is an XRD graph of Example 14, according to embodiments shown and described herein.

Example 13 was prepared by first suspending 5.0 g of fumed silica in 80 g of $H_2O$. Then, 0.241 g of NaOH in 5 ml of $H_2O$ followed by 13.0 g of TEAOH (35% aqueous) were both added to the fumed silica. The mixture was stirred vigorously for 30 minutes. In a separate beaker, 1.04 g of $Al(NO_3)_3 \cdot 9H_2O$ was dissolved in 5 g of $H_2O$ and the resulting solution was added to the suspended fumed silica mixture. The mixture was stirred for 30 minutes. Then, 270 mg of CNC was suspended in 10 g of $H_2O$ and homogenized using LabRam at 50% intensity (56 G acceleration) for 5 min. The suspension was added to the mixture and stirred for 90 minutes. The volatiles were removed on a rotary evaporator with a bath heated to 60° C. The resulting glass-like gel powder was transferred into a 25 ml PTFE beaker and placed on top of a Teflon rod into a 125 mL acid digestion bomb. The bomb was charged with 20 ml of water, sealed, and heated to 150° C. for 40 hours. The brown solids were washed with water (3 rinses using 80 mL each) using an ultracentrifuge, then dried at 100° C. for 7 h. The off-white solids were calcined at 550° C. for 8 h. The calcined solids were suspended in 1M $NH_4Cl$ solution (at a ratio of 10 ml of $NH_4Cl$ to 1 g of zeolite) at 90° C. overnight. The solids were isolated by centrifugation and the exchange was repeated twice. The solids were washed with water (4 rinses using 80 mL each) and dried at 60° C. overnight. Finally, the solids were calcined at 550° C. for 6 h. FIG. 7B is an XRD of Example 14. The properties of Examples 9-14 are listed in Table 3.

TABLE 3

Examples 9-12 with Varying Si/Al Ratios and Varying CNC Composition

| Property | Example 9 | Example 10 | Example 11 | Example 12 | Example 13 | Example 14 |
|---|---|---|---|---|---|---|
| Si/Al Ratio | 30 | 30 | 30 | 30 | 60 | 30 |
| CNC Type | Freeze-Dried | Commercial | Freeze-Dried | Commercial | Freeze-Dried | Freeze-Dried |
| CNC wt. % | 5 | 5 | 10 | 10 | 10 | 2.5 |
| BET Surface Area ($m^2$/g) | 640.2 | 644.2 | 600.4 | 476.33 | 519.6 | 535.6 |
| t-Plot Micropore Area ($m^2$/g) | 463.3 | 473.2 | 407.5 | 302.20 | 349.7 | 341.7 |
| t-Plot External Surface Area ($m^2$/g) | 176.9 | 171.0 | 192.9 | 174.1 | 169.9 | 196.9 |
| t-Plot Micropore Volume ($cm^3$/g) | 0.174 | 0.178 | 0.151 | 0.111 | 0.130 | 0.127 |
| BJH Adsorption cumulative surface area of pores between 17 Å and 3,000 Å diameter ($m^2$/g) | 139.3 | 159.4 | 138.1 | 120.5 | 147.8 | 161.5 |
| BJH Adsorption cumulative volume of pores between 17 Å and 3,000 Å diameter ($cm^3$/g) | 0.415 | 0.303 | 0.552 | 0.520 | 0.756 | 0.735 |
| BJH Adsorption average pore diameter (4 V/A)(Å) | 119.1 | 76.0 | 159.8 | 172.5 | 204.7 | 182.2 |

As shown and described, the mesoporous zeolites produced by the methods of the present disclosure exhibit high surface area, high micropore volume, and high crystallinity, indicating increased catalytic activity and an effective catalyst. Moreover, the mesoporous zeolites produced may have an average pore size of 20 nm, significantly larger than conventional zeolite pore size, as well as high mesopore volumes, allowing for the upgrading of larger molecules.

In addition to having a greater average pore size as well as high mesopores volumes, mesoporous zeolites produced by the methods of the present disclosure exhibit better crystallinity than commercially available zeolite beta. The crystallinity of each of Example 1-14 were measured as a percentage of the crystallinity of a comparative zeolite Beta, commercially available from Tosoh (HSZ-941HOA), by x-ray diffraction.

TABLE 4

Crystallinity of Examples 1-8

| Sample | XRD Crystallinity |
|---|---|
| Example 1 | 97% |
| Example 2 | 90% |
| Example 3 | 93% |
| Example 4 | 109% |
| Example 5 | 92% |
| Example 6 | 91% |
| Example 7 | 98% |
| Example 8 | 100% |
| Example 9 | 61% |
| Example 10 | 69% |
| Example 11 | 52% |
| Example 12 | 55% |
| Example 13 | 55% |
| Example 14 | 57% |

The relatively high crystallinity of the synthesized mesoporous zeolites, shown in Table 4, indicates a high degree of microporosity, which demonstrates that introduction of mesopores does not compromise the microporous structure of the zeolites. A high degree of microporosity of the synthesized zeolites is confirmed by high micropore volumes determined through physisorption experiments. High microporosity and crystallinity correlate with high catalytic activity, since catalytically active sites are located within the crystalline framework of the zeolite material.

The catalytic activity of the synthesized zeolites may further be quantified by measuring the products produced in mesitylene alkylation. Upon, alkylation, with benzyl alcohol, mesitylene is converted into 1,3,5-trimethyl-2-benzylbenzene. In a parallel reaction, benzyl alcohol can undergo condensation to form dibenzyl ether. Mesoporous zeolites provide significantly more catalytically active sites accessible to both mesitylene and benzyl alcohol than microporous zeolites, which results in higher catalytic conversions in the alkylation reaction.

The catalytic activities of Examples 9-14 and a comparative commercially available zeolite beta from Tosoh (HSZ-941HOA) were tested by first weighing 100 mg of each zeolite into a 40 mL vial. Next, 9.565 mL of mesitylene and dodecane (0.227 mL, 2.0 mmol) were added to each 40 mL vial. Then, the mixtures were stirred for 1 hour at 90° C. Next, the mixtures were heated to 120° C. and then benzyl alcohol (0.208 mL, 1.0 mmol) was added to the solutiuons. Aliquotes of 0.1 mL were then drawn after 105 minutes and subsequently diluted with 3 mL of toluene. The samples were then filtered with a syringe filter and analyzed by gas chromatography-mass spectrometry (GC-MS). Using the dodecane internal standard, the percentage of benzyl alcohol that was converted to the two products, dibenzyl ether and 1,3,5-trimethyl-2-benzylbenzene, was calculated. These conversion percentage data are shown in Table 5.

TABLE 5

Catalytic Activity of Produced Mesoporous Zeolites in Mesitylene Alkylation

| Sample | CNC Type | CNC wt. % | Si/Al Ratio | Benzyl Alcohol Conversion % |
|---|---|---|---|---|
| Commercial Zeolite Beta | N/A | N/A | 20 | 44 |
| Example 9 | Freeze-Dried | 10 | 30 | 75 |
| Example 10 | Commercial | 10 | 30 | 76 |
| Example 11 | Freeze-Dried | 5 | 30 | 68 |
| Example 12 | Commercial | 5 | 30 | 85 |
| Example 13 | Freeze-Dried | 10 | 60 | 80 |
| Example 14 | Freeze-Dried | 2.5 | 30 | 93 |

For the purposes of describing and defining the present disclosure it is noted that the term "about" is utilized in this disclosure to represent the inherent degree of uncertainty that may be attributed to any quantitative comparison, value, measurement, or other representation. The term "about" are also utilized in this disclosure to represent the degree by which a quantitative representation may vary from a stated reference without resulting in a change in the basic function of the subject matter at issue. Additionally, the term "consisting essentially of" is used in this disclosure to refer to quantitative values that do not materially affect the basic and novel characteristic(s) of the disclosure. For example, a chemical stream "consisting essentially" of a particular chemical constituent or group of chemical constituents should be understood to mean that the stream includes at least about 99.5% of a that particular chemical constituent or group of chemical constituents.

It is noted that one or more of the following claims utilize the term "where" as a transitional phrase. For the purposes of defining the present technology, it is noted that this term is introduced in the claims as an open-ended transitional phrase that is used to introduce a recitation of a series of characteristics of the structure and should be interpreted in like manner as the more commonly used open-ended preamble term "comprising."

It should be understood that any two quantitative values assigned to a property may constitute a range of that property, and all combinations of ranges formed from all stated quantitative values of a given property are contemplated in this disclosure.

Having described the subject matter of the present disclosure in detail and by reference to specific embodiments, it is noted that the various details described in this disclosure should not be taken to imply that these details relate to elements that are essential components of the various embodiments described in this disclosure, even in cases where a particular element is illustrated in each of the drawings that accompany the present description. Rather, the claims appended hereto should be taken as the sole representation of the breadth of the present disclosure and the corresponding scope of the various embodiments described in this disclosure. Further, it will be apparent that modifications and variations are possible without departing from the scope of the appended claims.

Several example aspects of the present disclosure are included below. In a first aspect, a method for producing a mesoporous zeolite comprises mixing a silicon-containing material, an aluminum-containing material, or both, with at least a quaternary amine and at least one base to produce a zeolite precursor solution; combining a nanocellulose mesopore template with the zeolite precursor solution to produce a zeolite precursor gel; crystallizing the zeolite precursor gel to produce a crystalline zeolite intermediate; and calcining the crystalline zeolite intermediate to produce the mesoporous zeolite.

In a second aspect, the first aspect may further comprise removing at least a solvent from the precursor gel prior to the crystallizing.

A third aspect may include the first or second aspect, wherein the crystallization comprises contacting the zeolite precursor gel with steam.

A fourth aspect may include any of the first to third aspects, wherein the crystalline zeolite intermediate is calcined by exposure to a temperature of at least 500° C.

A fifth aspect may include any of the first to fourth aspects, wherein the nanocellulose mesopore template comprises at least one of cellulose nanocrystals, nanocellulose fibers, or combinations thereof.

A sixth aspect may include any of the first to fifth aspects, wherein the silicon-containing material comprises $SiO_2$, sodium silicate, tetramethylsiloxane, tetraethylsiloxane, silicon salt, silicon alkoxide, or combinations thereof.

A seventh aspect may include any of the first to sixth aspects, wherein the aluminum-containing material comprises aluminum nitrate, aluminum sulfate, aluminum alkoxide, other aluminum salts, or combinations thereof.

An eighth aspect may include any of the first to seventh aspects, wherein the quaternary amine comprises tetraethylammonium hydroxide, tetraethylamonnium alkoxide, tetrapropylammonium alkoxide, other alkaline materials comprising ammonium, or combinations thereof.

A ninth aspect may include any of the first to eighth aspects, wherein the at least one base comprises an alkali metal hydroxide or an alkaline earth metal hydroxide.

A tenth aspect may include any of the first to ninth aspects, wherein the at least one base comprises sodium hydroxide, lithium hydroxide, and potassium hydroxide.

An eleventh aspect may include any of the first to tenth aspects, wherein the mesoporous zeolite has a crystallinity of at least 50% as measured using x-ray diffraction.

A twelfth aspect may include any of the first to eleventh aspects, wherein the mesoporous zeolite comprises a surface area of greater than or equal to 400 $cm^2/g$.

A thirteenth aspect may include any of the first to twelfth aspects, wherein the mesoporous zeolite comprises a micropore volume of greater than 0.1 mL/g and a mesopore volume of greater than 0.3 mL/g.

A fourteenth aspect may include any of the first to thirteenth aspects, wherein the mesoporous zeolite comprises an average mesopore size of greater than 3 nanometers.

A fifteenth aspect may include any of the first to fourteenth aspects, wherein the nanocellulose is a colloidal suspension of cellulose nanocrystals, nanocellulose fibers, or combinations thereof.

A sixteenth aspect may include any of the first to fifteenth aspects, wherein the mesoporous zeolite comprises an MFI framework type, a FAU framework type, an MOR framework type, or a BEA framework type.

A seventeenth aspect may include any of the first to sixteenth aspects, wherein the mesoporous zeolite is a zeolite Y.

An eighteenth aspect may include any of the first to seventeenth aspects, wherein the mesoporous zeolite is a ZSM-5 zeolite.

A nineteenth aspect may include any of the first to eighteenth aspects, wherein the mesoporous zeolite is a TS-1 zeolite.

A twentieth aspect may include any of the first to nineteenth aspects, wherein the mesoporous zeolite is a mordenite zeolite.

A twenty-first aspect may include any of the first to twentieth aspects, wherein the mesoporous zeolite is a silicalite-I zeolite.

A twenty-second aspect may include any of the first to twenty-first aspects, wherein the mesoporous zeolite comprises an aluminosilicate material and has a molar ratio of Si to Al of greater than or equal to 10.

A twenty-third aspect may include any of the first to twenty-second aspects, wherein the mesoporous zeolite comprises an aluminosilicate material and has a molar ratio of Si to Al of greater than or equal to 30.

According to a twenty-fourth aspect, a method for producing a mesoporous zeolite comprises mixing a silicon-containing material, an aluminum-containing material, or both, with at least a quaternary amine and at least one base to produce a zeolite precursor solution; combining a nanocellulose mesopore template with the zeolite precursor solution to produce a zeolite precursor gel, wherein the nanocellulose mesopore template comprises at least one of cellulose nanocrystals, nanocellulose fibers, or combinations thereof; crystallizing the zeolite precursor gel to produce a crystalline zeolite intermediate, wherein the crystallization comprises contacting the zeolite precursor gel with steam; and calcining the crystalline zeolite intermediate to produce the mesoporous zeolite, wherein the crystalline zeolite intermediate is calcined by exposure to a temperature of at least 500° C.

A twenty-fifth aspect may include the twenty-fourth aspect, wherein the nanocellulose mesopore template comprises cellulose nanocrystals.

A twenty-sixth aspect may include the twenty-fourth or twenty-fifth aspects, wherein the nanocellulose mesopore template comprises nanocellulose fibers.

What is claimed is:

1. A method for producing a mesoporous zeolite, the method comprising:
   mixing a silicon-containing material, an aluminum-containing material, or both, with at least a quaternary amine and at least one base to produce a zeolite precursor solution;
   combining a nanocellulose mesopore template with the zeolite precursor solution to produce a zeolite precursor gel;
   crystallizing the zeolite precursor gel to produce a crystalline zeolite intermediate; and
   calcining the crystalline zeolite intermediate to produce the mesoporous zeolite.

2. The method of claim 1, further comprising removing at least a solvent from the precursor gel prior to the crystallizing.

3. The method of claim 1, wherein the crystallization comprises contacting the zeolite precursor gel with steam.

4. The method of claim 1, wherein the crystalline zeolite intermediate is calcined by exposure to a temperature of at least 500° C.

5. The method of claim 1, wherein the nanocellulose mesopore template comprises at least one of cellulose nanocrystals, nanocellulose fibers, or combinations thereof.

6. The method of claim 1, wherein the silicon-containing material comprises $SiO_2$, sodium silicate, tetramethylsiloxane, tetraethylsiloxane, silicon salt, silicon alkoxide, or combinations thereof.

7. The method of claim 1, wherein the aluminum-containing material comprises aluminum nitrate, aluminum sulfate, aluminum alkoxide, other aluminum salts, or combinations thereof.

8. The method of claim 1, wherein the quaternary amine comprises tetraethylammonium hydroxide, tetraethylammonium alkoxide, tetrapropylammonium alkoxide, other alkaline materials comprising ammonium, or combinations thereof.

9. The method of claim 1, wherein the at least one base comprises an alkali metal hydroxide or an alkaline earth metal hydroxide.

10. The method of claim 1, wherein the at least one base comprises sodium hydroxide, lithium hydroxide, and potassium hydroxide.

11. The method of claim 1, wherein the mesoporous zeolite has a crystallinity of at least 50% as measured using x-ray diffraction.

12. The method of claim 1, wherein the mesoporous zeolite comprises a surface area of greater than or equal to 400 $cm^2/g$.

13. The method of claim 1, wherein the mesoporous zeolite comprises a micropore volume of greater than 0.1 mL/g and a mesopore volume of greater than 0.3 mL/g.

14. The method of claim 1, wherein the mesoporous zeolite comprises an average mesopore size of greater than 3 nanometers.

15. The method of claim 1, wherein the nanocellulose is a colloidal suspension of cellulose nanocrystals, nanocellulose fibers, or combinations thereof.

16. The method of claim 1, wherein the mesoporous zeolite comprises an MFI framework type, a FAU framework type, an MOR framework type, or a BEA framework type.

17. The method of claim 1, wherein the mesoporous zeolite is a zeolite Y.

18. The method of claim 1, wherein the mesoporous zeolite is a ZSM-5 zeolite.

19. The method of claim 1, wherein the mesoporous zeolite is a TS-1 zeolite.

20. The method of claim 1, wherein the mesoporous zeolite is a mordenite zeolite.

21. The method of claim 1, wherein the mesoporous zeolite is a silicalite-I zeolite.

22. The method of claim 1, wherein the mesoporous zeolite comprises an aluminosilicate material and has a molar ratio of Si to Al of greater than or equal to 10.

23. The method of claim 1, wherein the mesoporous zeolite comprises an aluminosilicate material and has a molar ratio of Si to Al of greater than or equal to 30.

24. A method for producing a mesoporous zeolite, the method comprising:
   mixing a silicon-containing material, an aluminum-containing material, or both, with at least a quaternary amine and at least one base to produce a zeolite precursor solution;
   combining a nanocellulose mesopore template with the zeolite precursor solution to produce a zeolite precursor gel, wherein the nanocellulose mesopore template comprises at least one of cellulose nanocrystals, nanocellulose fibers, or combinations thereof;
   crystallizing the zeolite precursor gel to produce a crystalline zeolite intermediate, wherein the crystallization comprises contacting the zeolite precursor gel with steam; and calcining the crystalline zeolite intermediate to produce the mesoporous zeolite, wherein the crystalline zeolite intermediate is calcined by exposure to a temperature of at least 500° C.

25. The method of claim 24, wherein the nanocellulose mesopore template comprises cellulose nanocrystals.

26. The method of claim 24, wherein the nanocellulose mesopore template comprises nanocellulose fibers.

\* \* \* \* \*

UNITED STATES PATENT AND TRADEMARK OFFICE
CERTIFICATE OF CORRECTION

| | |
|---|---|
| PATENT NO. | : 10,272,418 B2 |
| APPLICATION NO. | : 15/670686 |
| DATED | : April 30, 2019 |
| INVENTOR(S) | : Tatiana Pilyugina |

It is certified that error appears in the above-identified patent and that said Letters Patent is hereby corrected as shown below:

On the Title Page

Page 2, Column 1, item (56), references cited, other publications, cite no. 1, delete "Sunthesis" and insert --Synthesis--, therefor.

Page 2, Column 2, item (56), references cited, other publications, cite no. 3, delete "Habib" and insert --Habibi--, therefor.

Signed and Sealed this
Sixth Day of August, 2019

Andrei Iancu
*Director of the United States Patent and Trademark Office*